United States Patent [19]

Roth et al.

[11] Patent Number: 5,015,644
[45] Date of Patent: May 14, 1991

[54] ANTIHYPERLIPIDEMIC AND ANTIATHEROSCLEROTIC UREA AND CARBAMATE COMPOUNDS

[75] Inventors: Bruce D. Roth, Ann Arbor; Bharat K. Trivedi, Canton, both of Mich.

[73] Assignee: Warner-Lambert Company, Morris Plains, N.J.

[21] Appl. No.: 359,830

[22] Filed: Jun. 1, 1989

Related U.S. Application Data

[63] Continuation-in-part of Ser. No. 282,167, Dec. 9, 1988, abandoned, which is a continuation-in-part of Ser. No. 147,037, Feb. 5, 1988, abandoned, which is a continuation-in-part of Ser. No. 57,576, Jun. 2, 1987, abandoned.

[51] Int. Cl.$^5$ .................. A61K 31/17; C07C 275/28; C07C 275/30; C07C 275/32
[52] U.S. Cl. .................. 514/247; 514/255; 514/256; 514/307; 514/311; 514/357; 514/367; 514/372; 514/374; 514/378; 514/381; 514/383; 514/400; 514/406; 514/415; 514/427; 514/438; 514/443; 514/469; 514/471; 514/481; 514/488; 514/510; 514/513; 514/517; 514/542; 514/564; 514/585; 514/586; 514/587; 514/595; 514/596; 514/597; 514/598; 544/224; 544/335; 544/336; 546/146; 546/175; 546/332; 548/178; 548/214; 548/236; 548/247; 548/262.8; 548/253; 548/342; 548/378; 548/469; 548/560; 564/26; 564/27; 564/28; 564/29; 564/48; 564/50; 564/52; 564/53; 564/54; 549/58; 549/77; 549/471; 549/496; 558/57; 558/234; 560/10; 560/13; 560/20; 560/21; 560/22; 560/23; 560/28; 560/29; 560/31; 560/32; 560/34; 562/427; 562/430; 562/435; 562/437; 562/439
[58] Field of Search .................. 564/48, 26, 27, 28, 564/29, 50, 52, 53, 54; 514/596, 595, 597, 598, 247, 255, 256, 307, 311, 357, 367, 372, 374, 378, 381, 383, 400, 415, 427, 438, 443, 469, 471, 510, 517, 542, 564, 585, 586, 587; 544/224, 335, 336; 546/146, 175, 332; 548/178, 214, 236, 247, 262.8, 253, 342, 378, 469, 560; 549/58, 77, 471, 496; 558/57; 560/10, 13, 21, 22, 34; 562/427, 430, 435, 437, 439

[56] References Cited

U.S. PATENT DOCUMENTS

| | | | |
|---|---|---|---|
| 3,852,343 | 12/1974 | Krapcko | 564/56 |
| 4,387,105 | 6/1983 | DeVries et al. | 564/498 |
| 4,397,868 | 8/1983 | DeVries | 564/48 |
| 4,410,697 | 10/1983 | Torak et al. | 564/48 |
| 4,623,662 | 11/1986 | DeVries | 514/596 |

FOREIGN PATENT DOCUMENTS 049538 4/1982 European Pat. Off. .
154216 3/1982 German Democratic Rep. .

Primary Examiner—Richard L. Raymond
Attorney, Agent, or Firm—Ruth H. Newtson

[57] ABSTRACT

Certain substituted urea, thiourea, carbamate, and thiocarbamate compounds are potent inhibitors of the enzyme acyl-CoA: cholesterol acyltransferase and are thus useful agents for inhibiting the intestinal absorption of cholesterol, and for lowering blood plasma cholesterol.

31 Claims, No Drawings

ANTIHYPERLIPIDEMIC AND ANTIATHEROSCLEROTIC UREA AND CARBAMATE COMPOUNDS

CROSS-REFERENCE

This application is a continuation-in-part of co-pending application Ser. No. 282,167, filed Dec. 9, 1988, now abandoned, which is a continuation-in-part of co-pending application Ser. No. 147,037, filed Feb. 5, 1988, now abandoned, which is a continuation-in-part of co-pending application Ser. No. 057,576, filed June 2, 1987, now abandoned.

BACKGROUND OF THE INVENTION

This invention relates to chemical compounds having pharmacological activity, to pharmaceutical compositions which include these compounds, and to a pharmaceutical method of treatment. More particularly, this invention concerns certain substituted urea and carbamate compounds which inhibit the enzyme acyl-coenzyme A:cholesterol acyl-transferase (ACAT), pharmaceutical compositions containing these compounds, and a method of inhibiting intestinal absorption of cholesterol or of regulating cholesterol.

In recent years the role which elevated blood plasma levels of cholesterol plays in pathological conditions in man has received much attention. Deposits of cholesterol in the vascular system have been indicated as causative of a variety of pathological conditions including coronary heart disease.

Initially, studies of this problem were directed toward finding therapeutic agents which would be effective in lowering total serum cholesterol levels. It is now known that cholesterol is transported in the blood in the form of complex particles consisting of a core of cholesterol esters plus triglycerides and an exterior consisting primarily of phospholipids and a variety of types of protein which are recognized by specific receptors. For example, cholesterol is carried to the sites of deposit in blood vessels in the form of low density lipoprotein cholesterol (LDL cholesterol) and away from such sites of deposit by high density lipo-protein cholesterol (HDL cholesterol).

Following these discoveries, the search for therapeutic agents which control serum cholesterol turned to finding compounds which are more selective in their action; that is, agents which are effective in elevating the blood serum levels of HDL cholesterol and/or lowering the levels of LDL cholesterol. While such agents are effective in moderating the levels of serum cholesterol, they have little or no effect on controlling the initial absorption of dietary cholesterol in the body through the intestinal wall.

In intestinal mucosal cells, dietary cholesterol is absorbed as free cholesterol which must be esterified by the action of the enzyme acyl-CoA: cholesterol acyl-transferase (ACAT) before it can be packaged into the chylomicrons which are then released into the blood stream. Thus, therapeutic agents which effectively inhibit the action of ACAT prevent the intestinal absorption of dietary cholesterol into the blood stream or the reabsorption of cholesterol which has been previously released into the intestine through the body's own regulatory action.

INFORMATION DISCLOSURE

U.S. Pat. No. 4,397,868 (De Vries) discloses phenylurea compounds useful in reducing cholesterol wherein one of the nitrogen atoms is disubstituted with, e.g., aliphatic, alicyclic or aromatic groups.

U.S. Pat. No. 4,410,697 (Torok) discloses an improved process for preparing phenylurea compounds which are useful as herbicides, rodenticides, bacteriostatic agents, coccidiostatic agents and antiseptic agents. The non-aniline nitrogen in these compounds can be mono- or di-substituted with alkyl, cycloalkyl, alkoxy or phenyl which groups may be further substituted.

U.S. Pat. No. 4,623,662 (De Vries) discoses phenylurea and phenylthiourea compounds useful in treating atherosclerosis wherein the non-aniline nitrogen is di-substituted with aliphatic, cycloalkylalkyl, aralykyl groups wherein the aryl moiety may be substituted and wherein the aniline phenyl moiety is substituted with a wide variety of groups.

SUMMARY OF THE INVENTION

The present invention provides a class of compounds with ACAT inhibitory activity having the structure

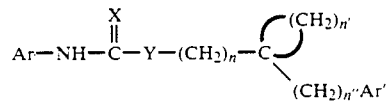

wherein Ar is phenyl or naphthyl. The phenyl or naphthyl group is unsubstituted, or may be optionally substituted with alkyl of from one to six carbon atoms, hydroxy, phenoxy, alkoxy of from one to six carbon atoms, fluorine, chlorine, bromine, nitro, trifluoromethyl, —COOH, —COO-alkyl (where alkyl is from one to four carbon atoms), or —NR$_1$R$_2$ in which R$_1$ and R$_2$ are independently hydrogen or alkyl of from one to six carbon atoms.

The atom X is oxygen or sulfur, Y is oxygen or —NH—, n is zero or is an integer of from one to three, n' is an integer of from two to six, and n'' is zero, one, or two.

Ar' is selected from phenyl, naphthyl, or a 5- or 6-membered monocyclic or fused bicyclic heterocycle. Ar' is unsubstituted, or may be optionally substituted with alkyl of from one to six carbon atoms; hydroxy; alkoxy of from one to six carbon atoms; benzyloxy; fluorine; chlorine; bromine; nitro; trifluoromethyl; —NH—COCH$_3$; —CONH$_2$; —COOH; —COO-alkyl (where alkyl is from one to four carbon atoms); —CH$_2$COOH; —CH$_2$CONH$_2$; —NR$_1$R$_2$ in which R$_1$ and R$_2$ are independently hydrogen, alkyl of from one to six carbon atoms which terminal carbon may contain an OR$_3$ group where R$_3$ is hydrogen, alkyl of from one to six carbon atoms, alkanoyl having from two to five carbon atoms, benzoyl, or when joined together form a 5- or 6-membered ring optionally interrupted by an oxygen atom or —NR$_3$' wherein R$_3$ is as defined above; —CH$_2$NR$_1$R$_2$ where R$_1$ and R$_2$ are as defined above; —CH$_2$OR$_3$ where R$_3$ is as defined above; —COO-alkyl where alkyl is from one to six carbons which terminal carbon may contain an OR$_3$ group or NR$_1$R$_2$ where R$_1$, R$_2$, and R$_3$ are as defined above; —NH—(CH$_2$)—COO-alkyl (where alkyl is from one to four carbon atoms); —SO$_2$NR$_1$R$_2$ where R$_1$ and R$_2$ are as defined above; —SO$_2$OR$_3$ where R$_3$ is as defined above, or —N-

H—SO$_2$R$_4$ where R$_4$ is alkyl of one to four carbon atoms or phenyl.

DETAILED DESCRIPTION

The compounds of the present invention form a class of substituted ureas, thioureas, carbamates, and thiocarbamates having potent activity as inhibitors of the enzyme acyl CoA: cholesterol acyltransferase (ACAT). Preferred compounds of the present invention are the urea and thiourea compounds, with the urea compounds being most preferred.

In the urea compounds of the present invention, the first nitrogen atom is monosubstituted by an aromatic ring system selected from phenyl or naphthyl. The phenyl ring is unsubstituted or, alternatively, is substituted with one, two, or three groups selected independently from alkyl of from one to six carbon atoms, alkoxy of from one to six carbon atoms, hydroxy, fluorine, chlorine, bromine, nitro, trifluoromethyl, —COOH, —COO-alkyl (where alkyl is from one to four carbon atoms), or —NR$_1$R$_2$ in which R$_1$ and R$_2$ are independently hydrogen or alkyl of from one to six carbon atoms. Preferred compounds are those in which the aromatic ring system is phenyl or substituted phenyl.

In the urea and thiourea compounds of this invention, the second nitrogen atom is substituted with an aryl-substituted cycloalkyl ring which may be attached directly to the nitrogen atom, or may separated from the nitrogen atom by a bridging group of up to three methylene (i.e. —CH$_2$—) groups. The cycloalkyl ring is cyclopropyl, cyclobutyl, cyclopentyl, cyclohexyl, or cycloheptyl, with cyclopentyl and cyclohexyl being preferred.

The cycloalkyl ring is further substituted, at the same atom of attachment to the nitrogen of the urea moiety or the same atom of attachment to the methylene bridge, by an aryl group. This aryl group is unsubstituted phenyl, naphthyl, or a 5- or 6-membered monocyclic or fused bicyclic heterocycle or, alternatively, one of these aromatic rings may optionally be substituted by one, two, or three groups independently selected from alkyl of from one to six carbon atoms; alkoxy of from one to six carbon atoms; benzyloxy; hydroxy; fluorine; chlorine;

35 bromine; nitro; trifluoromethyl; —NH—COCH$_3$; —CONH$_2$; —COOH; —CH$_2$COOH; —CH$_2$CONH$_2$; —NR$_1$R$_2$ in which R$_1$ and R$_2$ are independently hydrogen, alkyl of from one to six carbon atoms which terminal carbon may contain an OR$_3$ group where R$_3$ is hydrogen or alkyl of from one to six carbon atoms, or when joined together form a 5- or 6-membered ring optionally interrupted by an oxygen atom or —NR$_3$; —CH$_2$NR$_1$R$_2$ where R$_1$ and R$_2$ are as defined above; —CH$_2$OR$_3$ where R$_3$ is as defined above; —COO-alkyl where alkyl is from one to six carbons which terminal carbon may optionally be substituted with an OR$_3$ group or NR$_1$R$_2$ where R$_1$, R$_2$, and R$_3$ are as defined above; —NH—(CH$_2$)—COO-alkyl (where alkyl is from one to four carbon atoms); —SO$_2$NR$_1$R$_2$ where R$_1$ and R$_2$ are as defined above; —SO$_2$OR$_3$ where R$_3$ is as defined above, or —NH—SO$_2$R$_4$ where R$_4$ is alkyl of one to four carbon atoms or phenyl.

A 5- or 6-membered monocyclic or fused bicyclic heterocycle is a monocyclic or fused bicyclic aromatic ring containing at least one to four hetero atoms in at least one ring, such as nitrogen, oxygen or sulfur or a combination thereof. Such a heterocycle group includes, for example, thienyl, benzothienyl, furanyl, benzofuranyl, pyridyl, pyrimidinyl, pyridazinyl, pyrazinyl, pyrrolyl, pyrrazolyl, isothiazolyl, oxazolyl, isoxazolyl, triazolyl, tetrazolyl, imidazolyl, benzothiazolyl, indolyl, quinolinyl, isoquinolinyl, or N-oxides of a heterocycle containing a nitrogen atom.

More specifically, such a heterocycle may be 2- or 3-thienyl; 2- or 3-furanyl; 2-, 3-, or 4-pyridyl or or 3-thienyl; 2- or 3-furanyl; 2-, 3-, or 4-pyridyl or -pyridyl-N-oxide; 2, 4, or 5-pyrimidinyl; 3- or 4-pyradazinyl; 2-pyrazinyl; 2- or 3-pyrrolyl; 3-, 4-, or 5-pyrrazolyl, 3-, 4-, or 5-isoxazolyl; 3-, 4- or 5-oxazolyl; 3-, 4-, or 5-isothiazolyl; 5-tetrazolyl; 3- or 5-(1,2,4-)triazolyl; 4- or 5-(1,2,3-)triazolyl; 2-, 4-, or 5-imidazolyl; 2-, 3-, 4-, 5-, 6-, or 7-indolyl; 2-, 3-, 4-, 5-, 6-, 7-, or 8-quinolinyl; 1-, 3-, 4-, 5-, 6-, 7-, or 8-isoquinolinyl; 2-, 4-, 5-, 6-, or 7-benzothiazolyl; or 2-, 3-, 4-, 5-, 6-, or 7-benzothienyl.

A preferred class of urea compounds is represented by a compound of the formula

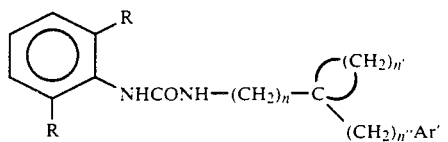

where R is alkyl of one to four carbon atoms, especially isopropyl or otherwise referred to as 1-methylethyl; n is 0 or 1, especially 1; n' is an integer from 2 to 6, especially 4 or 5; n" is 0 or 1, especially 0, and Ar' is phenyl or phenyl substituted by alkyl of from one to six carbon atoms; hydroxy; alkoxy of from one to six carbon atoms; benzyloxy; fluorine; chlorine; bromine; nitro; trifluoromethyl; —NH—COCH$_3$; —CONH$_2$; —COOH; —COO-alkyl (where alkyl is from one to four carbon atoms); —CH$_2$COOH; —CH$_2$CONH$_2$; —NR$_1$R$_2$ in which R$_1$ and R$_2$ are independently hydrogen, alkyl of from one to six carbon atoms which terminal carbon may contain an OR$_3$ group where R$_3$ is hydrogen or alkyl of from one to six carbon atoms, or when joined together form a 5- or 6-membered ring optionally interrupted by an oxygen atom or —NR$_3$; —CH$_2$NR$_1$R$_2$ where R$_1$ and R$_2$ are as defined above; —CH$_2$OR$_3$ where R$_3$ is as defined above; —COO-alkyl where alkyl is from one to six carbons which terminal carbon may contain an OR$_3$ group or NR$_1$R$_2$ where R$_1$, R$_2$, and R$_3$ are as defined above; —NH—(CH$_2$)—COO-alkyl (where alkyl is from one to four carbon atoms); —SO$_2$NR$_1$R$_2$ where R$_1$ and R$_2$ are as defined above; —SO$_2$OR$_3$ where R$_3$ is as defined above, or —NH—SO$_3$R$_4$ where R$_4$ is alkyl of one to four carbon atoms or phenyl. Especially preferred is a compound as defined above where Ar' is phenyl or phenyl substituted by alkyl, hydroxy, alkoxy, fluorine, chlorine, nitro, trifluoromethyl, or —NR$_1$R$_2$.

A particularly valuable class of urea compounds having a heterocyclic group defined above is a compound of the formula

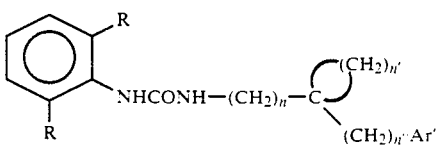

where R is alkyl of one to four carbon atoms, especially isopropyl or otherwise referred to as 1-methylethyl; n is 0 or 1, especially 1; n' is an integer from 2 to 6, especially 4 or 5; n" is 0 or 1, especially 0, and Ar' is a 5- or 6-membered monocyclic or fused bicyclic heterocycle defined above.

Preferred compounds of this invention are those in which the aromatic ring system attached to the cycloalkyl ring is thienyl, tetrazolyl, isoxazolyl, triazolyl, pyrazolyl, pyridyl, pyridyl-N-oxide, unsubstituted phenyl, or unsubstituted naphthyl.

Examples of compounds contemplated as falling within the scope of the invention are the following:

N-(2,6-Dimethylphenyl)-N'-(1-phenylcycopentyl)urea.
N-(2,6-Diethylphenyl)-N'-(1-phenylcyclobutyl)urea.
N-(2,6-Diethylphenyl)-N'-(1-phenylcyclopentyl)urea.
N-(2,6-Diethylphenyl)-N'-(1-phenylcyclopropyl)methyl]urea.
N-(1-Phenylcyclopentyl)-N'-(2,4,6-trimethoxyphenyl)urea.
N-(2,6-Dimethylphenyl)-N'-[1-(2-thienyl)cyclohexyl]urea.
N-(2,6-Diethylphenyl)-N'-[1-(2-thienyl)cyclohexyl]urea.
N-[2,6-bis(1-Methylethyl)]-N'-[1-(2-thienyl)cyclohexyl]urea.
N-(2,6-Diethylphenyl)-N'-[(1-phenylcyclohexyl)methyl]urea.
N-(2,6-Dimethylphenyl)-N'-(1-phenylcyclopentyl)methyl]urea.
N-(2,6-Dimethylphenyl)-N'-[(1-phenylcyclohexyl)methyl]urea.
N-(2,6-Diethylphenyl)-N'-[(1-phenylcyclopentyl)methyl]urea.
N-[2,6-bis(1-Methylethyl)phenyl]-N'-(1-phenylcyclopentyl)methyl]urea.
N-[2,6-bis(1-Methylethyl)phenyl]-N'-[(1-phenylcyclohexyl)methyl]urea.
N-[2-Methyl-6-(1-methylethyl)phenyl]-N'-1-(2-thienyl)cyclohexyl]urea.
N-[2-(1,1-Dimethylethyl)-6-methylphenyl]-N'-[1-(2-thienyl)cyclohexyl]urea.
N-[2-Methyl-6-(1-methylethyl)phenyl]-N'-[(1-phenylcyclohexyl)methyl]urea.
N-[2-(1,1-Dimethylethyl)-6-methylphenyl]-N'-[(1-phenylcyclohexyl)methylurea.
N-[2-Ethyl-6-(1-methylethyl)phenyl]-N'-[(1-phenylcyclohexyl)methyl]urea.
N-[2-Methyl-6-(1-methylethyl)phenyl]-N'-[(1-phenylcyclopentyl)methyl]urea.
N-[2-(1,1-Dimethylethyl)-6-methylphenyl]-N'-[(1-phenylcyclopentyl)methyl]urea.
N-[2-Ethyl-6-(1-methylethyl)phenyl]-N'-[(1-phenylcyclopentyl)methyl]urea.
N-(2,4-Difluorophenyl)-N'-[1-(2-thienyl)-cyclohexyl]urea.
N-(2,4-Difluorophenyl)-N'-[(1-phenylcyclopentyl)methyl]urea.
N-(2,4-Difluorophenyl)-N'-[(1-phenylcyclohexyl)methyl]urea.
N-(2,6-Dibromo-4-fluorophenyl)-N'-[(1-phenylcyclohexyl)methyl]urea.
N-(2,4-Dimethylphenyl)-N'-[(1-phenylcyclohexyl)methyl]urea.
2-[[[[(1Phenylcyclohexyl)methyl]amino]carbonyl]amino]benzoic acid, butyl ester.
N-[2,6-bis(1-Methylethyl)phenyl]-N'-[1-(2-naphthalenyl)cyclobutylmethyl]urea.
N-(2,5-Dimethylphenyl)-N'-(1-phenylcyclohexyl)methyl]urea.
N-(2,3-Dichlorophenyl)-N'-[(1-phenylcyclohexyl)methyl]urea.
N-(3,4-Dichlorophenyl)-N'-[(1-phenylcyclohexyl)methyl]urea.
N-[4-(1-Methylethyl)phenyl]-N'-[(1-phenylcyclohexyl)methyl]urea.
N-(4-Bromophenyl)-N'-(1-phenylcyclohexyl)methyl]urea.
N-(4-Butoxyphenyl)-N'-(1-phenylcyclohexyl)methyl]urea.
N-(4-Phenoxyphenyl)-N'-[(1-phenylcyclohexyl)methyl]urea.
N-(4-Nitrophenyl)-N'-[(1-phenylcyclohexyl)methyl]urea.
N-(4-Methoxyphenyl)-N'-[(1-phenylcyclohexyl)methyl]urea.
N-(4-Ethoxyphenyl)-N'-[(1-phenylcyclohexyl)methyl]urea.
N-(4-Acetylphenyl)-N'-[(1-phenylcyclohexyl)methyl]urea.
4-[[[(1-Phenylcyclohexyl)methyl]amino]carbonyl]amino]benzoic acid, ethyl ester.
N-(4-Methylphenyl)-N'-[(1-phenylcyclohexyl)methyl]urea.
N-(4-Ethylphenyl)-N'-[(1-phenylcyclohexyl)methyl]urea.
N-(3-Methoxyphenyl)-N'-[(1-phenylcyclohexyl)methyl]urea.
N-[(1-1,1'-Biphenyl]-4-ylcyclobutyl)methyl]N'-[2,6-bis(1-methylethyl)phenyl]urea.
N-(4-Chlorophenyl)-N'-(1-phenylcyclohexyl)methyl]urea.
N-(4-Iodophenyl)-N'-[(1-phenylcyclohexyl)methyl]urea.
N-(2-Methylphenyl)-N'-[(1-phenylcyclohexyl)methyl]urea.
N-(3-Methylphenyl)-N'-(1-phenylcyclohexyl)methyl]urea.
N-[2,6-bis(1-Methylethyl)phenyl]-N'-[[1-4-(trifluoromethyl)phenyl]cyclobutyl]methyl]urea.
N-[2,6-bis(1-Methylethyl)phenyl]-N'-[[1-(4-methylphenyl)cyclobutyl]methyl]urea.
N-[2,6-bis(1-Methylethyl)phenyl]-N'-[1-(2-methylphenyl)cyclobutyl]methyl]urea.
N-[2,6-bis(1-Methylethyl)phenyl]-N'-[1-(1-naphthalenyl)cyclobutyl]methylurea.
N-[2,6-bis(1-Methylethyl)phenyl]-N'-[1-(3-methylphenyl)cyclobutyl]methyl]urea.
N-[(1-Phenylcyclohexyl)methyl]-N'-3-(trifluoromethyl)phenylurea.
N-[2-Chloro-5-(trifluoromethyl)phenyl]-N'-(1-phenylcyclohexyl)methyl]urea.
N-(5-Chloro-2-methoxyphenyl)-N'-(1-phenylcyclohexyl)methyl]urea.
N-(4-Chloro-2-methylphenyl)-N'-[(1-phenylcyclohexyl)methyl]urea.
N-[2,6-bis(1-Methylethyl)phenyl]-N,-[[1-(3,4,5-trimethoxyphenyl)cyclobutyl]urea.
N-[2,6-bis(1-Methylethyl)phenyl]-N'-[[1-[3-(trifluoromethyl)phenyl]cyclobutyl]methyl]urea.
2-[[[[(1-Phenylcyclohexyl)methyl]amino]carbonyl]amino]benzoic acid, methyl ester.
2-[[[[(1-Phenylcyclohexyl)methyl]amino]carbonyl]amino]benzoic acid, ethyl ester.
N-Phenyl-N'-(1-phenylcyclohexyl)methyl]urea.
N-(2,5-Dimethoxyphenyl)-N'-(1-phenycyclohexyl)methyl]urea.

N-[2,6-bis(1-Methylethyl)phenyl]-N'-[1-2-(trifluoromethyl)phenyl]cyclobutyl]methyl]urea.
N-[2,6-bis(1-Methylethyl)phenyl]-N'-[[1-(4-methylphenyl)cyclopentyl]methyl]urea.
N-[2,6-bis(1-Methylethyl)phenyl]-N'-[1-[4-(1-methylethyl)phenyl]cyclopentyl]methyl]urea.
N-[2,6-bis(1-Methylethyl)phenyl]-N'-[1-(2-methylphenyl)cyclopentylmethyl]urea.
N-[2,6-bis(1-Methylethyl)phenyl]-N'-(1-phenylcyclopropyl)methyl]urea.
N-(5-Chloro-2-methylphenyl)-N'-[(1-phenylcyclohexyl)methyl]urea.
N-(2,5-Dichlorophenyl)-N'-[(1-phenylcyclohexyl)methyl]urea.
N-[2,6-bis(1-Methylethyl)phenyl]-N'-[[1-(4-methoxyphenyl)cyclopentyl]methylurea.
N-[2,6-bis(1-Methylethyl)phenyl]-N'-[(1-phenylcyclobutyl)methyl]urea.
N-[2,6-bis(1-Methylethyl)phenyl]-N'-[1-(2-naphthalenyl)cyclopentyl]methyl]urea.
N-[2,6-bis(1-Methylethyl)phenyl]-N'-[1-(2-naphthalenyl)cyclobutyl]methyl]urea.
N-[2,6-bis(1-Methylethyl)phenyl]-N'-[[1-[3-(phenylmethoxy)phenyl]cyclopentyl]methyl]urea.
N-[2,6-bis(1-Methylethyl)phenyl]-N'-[[1-(4-fluorophenyl)cyclopentyl]methyl]urea.
N-[2,6-bis(1-Methylethyl)phenyl]-N'-[[1-[4-(phenylmethoxy)phenyl]cyclopentyl]methyl]urea.
N-[2,6-bis(1-Methylethyl)phenyl]-N'-[[1-[4-(trifluoromethyl)phenyl]cyclopentyl]methyl]urea.
N-[2,6-bis(1-Methylethyl)phenyl]-N'-[[1-(2,6-dichlorophenyl)cyclobutyl]methyl]urea,
N-[2,6-bis(1-Methylethyl)phenyl]-N'-[[1-[3,5-bis(trifluoromethyl)phenyl]cyclopentyl]-methyl]urea.
N-[2,6-bis(1-Methylethyl)phenyl]-N'-[1-[2-(trifluoromethyl)phenyl]cyclopentyl]methyl]urea.
N-[2,6-bis(1-Methylethyl)phenyl]-N'-[[1-(4-chlorophenyl)cyclopentyl]methyl]urea.
N-[2,6-bis(1-Methylethyl)phenyl]-N'-[[1-(4-nitrophenyl)cyclopentyl]methyl]urea.
N-[1-(4-Aminophenyl)cyclopentyl]methyl]-N'-[2,6-bis(1-methylethyl)phenyl]urea.
N-[4-[1-[[[[[2,6-bis(1-Methylethyl)phenyl]amino]carbonyl]amino]methyl]cyclopentyl]phenyl]acetamide.
N-[2,6-bis(1-Methylethyl)phenYl]-N'-[[1-(4-dimethylaminophenyl)cyclopentyl]methyl]urea or its hydrochloride salt.
N-[2,6-bis(1-methylethyl)phenyl]-N'-[1-(4-dimethylaminophenyl)cyclohexyl]methyl]urea.
N-[2,6-bis(1-methylethylphenyl]-N'-[[1-(4-diethylaminophenyl)cyclopentyl]methyl]urea.
N-[2,6-bis(1-methylethyl)phenyl]-N'-[[[1-4-(2-hydroxyethyl)amino]phenyl]cyclopentyl]methyl]urea.
N'-[[1-[4-[-bis(2-hydroxyethylamino]phenyl]cyclopentyl]methyl]-N-[2,6-bis(1-methylethyl)phenyl]urea.
N-[2,6-bis(1-methylethyl)phenyl]-N'-[[[1-(2-trifluoromethyl-4-dimethylamino)phenyl]cyclopentyl]methyl]urea.
N-[2,6-bis(1-methylethyl)phenyl]-N'-[[[1-(2-trifluoromethyl-4-methylamino)phenyl]cyclopentyl]methyl]urea.

Additional examples of compounds contemplated as falling within the scope of the invention are the following N-(2,6-bis(1-methylethyl)-N'-[1-heterocyclecyclopentyl)methyl]ureas
where the heterocycle is:
5-(1-methyltetrazolyl),
5-(1-H-tetrazolyl),
4-(2,5-dimethylisoxazolyl),
4-[(1-benzyl-5-(N,N-dimethylamino)]-1,2,3-triazolyl],
4-[1-methyl-5-(N,N-dimethylamino)-1,2,3-triazolyl],
4-(1,3,5-trimethylpyrazolyl),
4-(1-H,-3,5-dimethylpyrazolyl), and
3-pyridyl-N-oxide.

By the term "lower alkyl" or "alkyl" as used throughout this specification and the appended claims is meant a branched or unbranched hydrocarbon grouping derived from a saturated hydrocarbon of from one to six carbon atoms by removal of a single hydrogen atom. Examples of alkyl groups contemplated as falling within the scope of this invention include methyl, ethyl, propyl, 1-methylethyl, butyl, 1-methylpropyl, 2-methylpropyl, and 1,1-dimethylethyl.

By the term "alkoxy" is meant a lower alkyl group, as defined above, attached to the parent molecular moiety through an oxygen atom.

In those instances where the compounds of the present invention bear a basic nitrogen atom as, for example, when Ar or Ar' is substituted by amino, alkylamino, or dialkylamino, or when Ar' is pyridyl, the compounds are capable of forming acid addition salts. These acid addition salts are also contemplated as falling within the scope of this invention.

While the acid addition salts may vary from the free base form of the compounds in certain properties such as melting point and solubility, they are considered equivalent to the free base forms for the purposes of this invention.

The acid addition salts may be generated from the free base forms of the compounds by reaction of the latter with one equivalent of a suitable non-toxic, pharmaceutically acceptable acids followed by evaporation of the solvent employed for the reaction and recrystallization of the salt, if required. The free base may be recovered from the acid addition salt by reaction of the salt with a water solution of the salt with a suitable base such as sodium carbonate, sodium bicarbonate, potassium carbonate, sodium hydroxide, and the like.

Suitable acids for forming acid addition salts of the compounds of this invention include, but are not necessarily limited to acetic, benzoic, benzenesulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The class of acids suitable for the formation of non-toxic, pharma-ceutically acceptable salts is well known to practi-tioners of the pharmaceutical formulation arts. (See, for example, Stephen N. Berge, et al. *J. Pharm. Sciences,* 66:1–19 (1977).

In those instances where the compounds of the present invention bear a basic nitrogen atom in a heterocyclic group as, for example, when Ar' is pyridyl, the compounds are capable of forming N-oxides. These N-oxides are also contemplated as falling within the scope of this invention.

The N-oxides may be prepared from the free base forms of the compounds by reaction of the latter with an oxidizing agent, such as, for example, hydrogen peroxide, peracetic acid or perbenzoic acid in a suitable solvent.

Further, the compounds of this invention may exist in unsolvated as well as solvated forms with pharma-ceutically acceptable solvents such as water, ethanol and the like. In general, the solvated forms are considered equivalent to the unsolvated forms for the purposes of this invention.

The compounds of the present invention are prepared by the general method outline in Reaction Scheme 1. The appropriately substituted isocyanate, 2a (where X=O), or thioisocyanate compounds, 2b (where X=S), are reacted with the desired amine, 3, to obtain the substituted urea compounds of the present invention, 1a-1b, or with the desired alcohol, 4, to obtain the substituted carbamate compounds of the present invention, 1c-1d.

The reaction is generally carried out in a polar aprotic organic solvent such as ethyl acetate, at any temperature between room temperature and the boiling point of the solvent, with room temperature being preferred.

The reaction is allowed to proceed until analysis of the mixture by a means such as chromatography indicates that the reaction is substantially complete. Reaction times may vary between about two hours to about 24 hours, depending upon the particular reagents and reaction temperature employed. The starting isocyanate or thioisocyanate compounds are known or commercially available or, if not previously known, are prepared by methods well known in the art from the corresponding amine compounds.

The amine compounds, 3, are prepared by the general method detailed in *J. Org. Chem.*, 36(9): 1308 (1971) and depicted schematically in Reaction Scheme 2. Referring to Reaction Scheme 2, phenylacetonitrile or the substituted phenylacetonitrile 5, is reacted with the desired alpha-omega dibromoalkalne, 6, in the presence of base to produce the cycloalkyl nitrile, 7. This compound is catalytically reduced by the action of hydrogen over a noble metal catalyst to produce the aryl(aminomethyl)-cycloalkane compound, 8. Acid hydrolyis of compound 6, produces the corresponding aryl(cycloalkyl) carboxamide, 9, which is then subjected to the Hofmann degradation reaction (Ber. 14: 2725 (1881)) to produce the aryl(cycloalkyl)amine 10.

Reaction Scheme 1

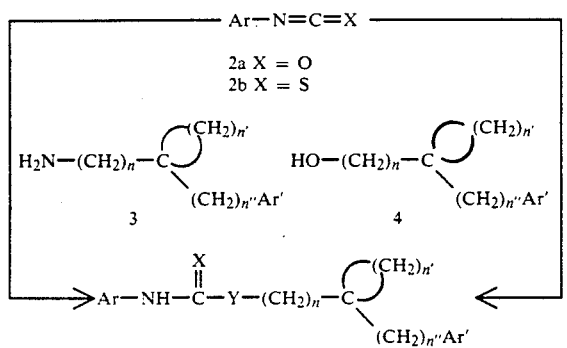

1a X = O, Y = NH
1b X = S, Y = NH
1c X = O, Y = O
1d X = S, Y = O

Reaction Scheme 2

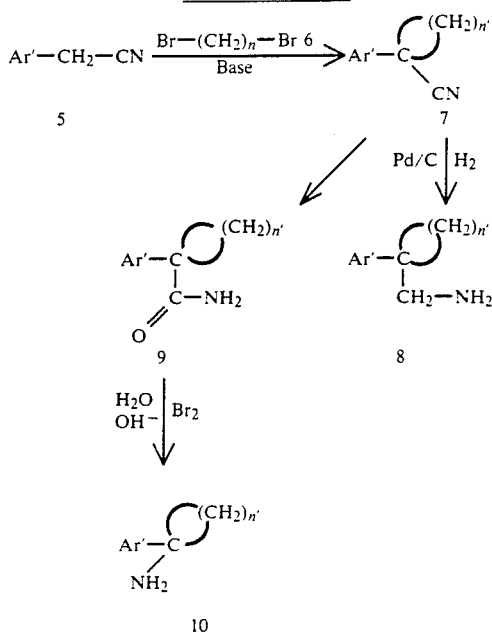

For the amines, where Ar' can be substituted with $-NR_1R_2$ where $R_1$ and $R_2$ are other than hydrogen as defined above, the intermediate 1-cyano-1-(4-nitrophenyl)cycloalkyl derivative is first reductively alkylated using Pd/c in the presence of appropriate aldehyde. This dialkylamino nitrile derivative is then reduced to the requisite amine (8) using Ra-Ni and hydrogen in methanolic ammonia preferably at room temperature. For compounds (I) where $R_1$ and $R_2$ may contain $OR_3$ where $R_3$ is hydrogen, the parent molecule where $R_1=R_2=H$ is reacted with electrophile such as ethylene oxide in an alcohol solution at reflex temperature. For compounds where the phenyl ring has more than one substituent (such as in example 93, 94), the required amine is prepared as follows: the 1-cyano-1-(2-trifluoromethyl)phenyl cyclopentane is first nitrated using fuming nitric acid at 5° C. to room temperature then reductively alkylated as described above. The nitrile derivative is then reduced to the corresponding amine (8) using Ra-Ni in methanolic ammonia. For compounds, where Ar' is substituted it is preferred to hydrolyse with —COOH, the corresponding ester derivative (I) using base such as sodium or potassium hydroxide.

As shown by the data presented below in Table 1, the compounds of the present invention are potent inhibitors of the enzyme acyl-CoA:cholesterol acyl-transferase (ACAT), and are thus effective in inhibiting the esterification and transport of cholesterol across the intestinal cell wall. The compounds of the present invention are thus useful in pharmaceutical formulations for the inhibition of intestinal absorption of dietary cholesterol, the reabsorption of cholesterol released into the intestine by normal body action, or the modulation of cholesterol.

IN VITRO TESTS

The ability of representative compounds of the present invention to inhibit ACAT was measured using an in vitro test more fully described in Field, F. J. and Salone, R. G., *Biochemica et Biophysica* 712: 557-570

(1982). The test assesses the ability of a test compound to inhibit the acylation of cholesterol by oleic acid by measuring the amount of radio-labeled cholesterol oleate formed from radio-labeled oleic acid in a tissue preparation containing rabbit intestinal microsomes.

The data appear in Table 1 where they are expressed as $IC_{50}$ values; i.e. the concentration of test compound required to inhibit 50% expression of the enzyme.

TABLE 1

| Compound of Example | $IC_{50}$ (Micromolar) |
| --- | --- |
| 1 | 0.08 |
| 2 | 0.23 |
| 3 | 0.12 |
| 4 | 0.088 |
| 5 | 0.70 |
| 6 | 0.13 |
| 7 | 0.048 |
| 8 | 0.043 |
| 9 | 0.051 |
| 10 | 0.154 |
| 11 | 0.081 |
| 12 | 0.015 |
| 13 | 0.017 |
| 14 | 0.021 |
| 15 | 0.23 |
| 16 | 0.256 |
| 17 | 0.058 |
| 18 | 0.054 |
| 19 | 0.020 |
| 20 | 0.016 |
| 21 | 0.018 |
| 22 | 0.025 |
| 23 | 0.37 |
| 24 | 1.28 |
| 25 | 0.79 |
| 26 | 0.039 |
| 87 | 0.051 |
| 88 | 0.052 |
| 89 | 0.048 |
| 90 | 0.035 |
| 91 | 0.025 |
| 92 | 0.021 |
| 93 | 0.050 |
| 94 | 0.057 |
| 95 | 0.097 |

IN VIVO TESTS

In one in vivo screen, designated PCC, male Sprague-Dawley rats (approximately 200 g body weight) are randomly divided into groups and provided ad libidum a regular chow diet (Purina No. 5002, Ralston Purina Co., 711 West Fuesser Road, Mascoutah, Ill., 62224, USA), supplemented with 5.5% peanut oil, 1.5% cholesterol, and 0.3%-0.5% cholic acid, together with 0.05% of the test drug which is admixed into the diet. After one week the animals are etherized and a blood sample is taken from the heart and mixed with 0.14% ethylene-diamine tetraacetic acid (EDTA) to measure the total cholesterol. The results of this trial for representative compounds of the present invention appear in Table 2.

TABLE 2

| Compound of Example | Total Blood Cholesterol (mg/dl) | % Change |
| --- | --- | --- |
| 13 | 61 | −73 |
|  | (Control = 224) |  |
| 8 | 60 | −69 |
|  | (Control = 181) |  |
| 87 | 61 | −69 |
|  | (Control = 194) |  |
| 88 | 70 | −64 |

TABLE 2-continued

| Compound of Example | Total Blood Cholesterol (mg/dl) | % Change |
| --- | --- | --- |
|  | (Control = 194) |  |

In therapeutic use as agents for the inhibition of intestinal absorption of cholesterol, or as hypolipidemic or hypocholesterolemic agents, the compounds utilized in the pharmaceutical method of this invention are administered to the patient at dosage levels of from 250 to 1000 mg per day. For a normal human adult of approximately 70 kg of body weight, this translates into a dosage of from 5 to 20 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

Powders and tablets preferably contain between about 5 to about 70% by weight of the active ingredient. Suitable carriers are magnesium carbonate, magnesium stearate, talc, lactose, sugar, pectin, dextrin, starch, tragacanth, methyl celulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid form preparations include solutions suitable for oral administration, or suspensions and emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

The following preparative examples are provided to enable one skilled in the art to practice the invention, and are illustrative thereof. They are not to be read as limiting the scope of the invention as it is defined by the appended claims.

EXAMPLE 1

Preparation of
N-(2,6-dimethylphenyl)-N'-(1-phenylcyclopentyl)urea

To a solution of 1-phenylcyclopentyl amine (1.0 gm, 0.006 mole) in 30 ml of ethylacetate, 2,6-dimethylphenyl isocyanate (0.91 g; 0.006 mole) is added and the reaction mixture is stirred at room temperature for 20 hours. Volatiles are removed under reduced pressure and the residue is crystallized from ethylacetate-hexane yielding 1.65 g of N-(2,6-dimethylphenyl-N'-(1-phenylcyclopentyl) urea having a melting point of 227°–229° C.

Analysis calculated for $C_{20}H_{24}N_2O$: C=77.88, H=7.84; N=9.08. Found C=77.72; H=7.83; N=9.19.

EXAMPLE 2

Preparation of
N-(2,6-diethylphenyl)-N,-(1-phenylcyclobutyl)urea

To a solution of 1-phenylcyclobutyl amine (1.0, 0.0057 mole) in 30 ml of ethylacetate, 2,6-diethylphenylisocyanate (0.84 g, 0.0057 mole) is added and the reaction mixture is stirred at room temperature for 20 hours. Precipitated solid is filtered, washed with ethylacetate and dried yielding 1.46 gm of N-(2, 6-diethylphenyl)-N'-(1-phenylcyclobutyl)urea having a melting point of 227°–230° C.

Analysis calculated for $C_{21}H_{26}N_2O$: C=78.22; H=8.12; N=8.68. Found C=78.43; H=8.32; N=8.89.

EXAMPLE 3

Preparation of
N-(2,6-diethylphenyl)-N'-(1-phenylcyclopentyl)urea

The title compound is prepared according to the procedure described for the Example 2. Melting point 215°–218° C.

Analysis calculated for $C_{22}H_{28}N_2O$: C=78.53; H=8.38; N=8.32. Found C=78.35, H=8.34; N=8.19.

EXAMPLE 4

Preparation of
N-(2,6-diethylphenyl)-N'-[(1-phenylcyclopropyl)methyl]urea

The title compound is prepared according to Example 2. Melting point 166°–168° C.

Analysis calculated for $C_{21}H_{26}N_2O$: C=78.22; H=8.12; N=8.68. Found C=78.13; H=8.28; N=8.63.

EXAMPLE 5

Preparation of
N-(1-phenylcyclopentyl)-N'-(2,4,6-trimethoxyphenyl)urea

The title compound is prepared according to Example 2. Melting point 193°–195° C.

Analysis is calculated for $C_{21}H_{26}N_2O_4$: C=68.09; H=7.07; N=7.56. Found C=67.75; H=6.85; N=7.34.

EXAMPLE 6

Preparation of
N-(2,6-dimethylphenyl)-N'-[1-(2-thienyl)cyclohexyl]urea

The title compound is prepared according to Example 2. Melting point 220°–222° C.

Analysis calculated for $C_{19}H_{24}N_2OS$: C=69.47; H=7.36; N=8.52, S=9.76. Found C=69.43; H=7.24; N=8.69; S=9.87.

EXAMPLE 7

Preparation of
N-(2,6-diethylphenyl)-N'-[1-(2-thienyl)cyclohexyl]urea

The title compound is prepared according to Example 2. Melting Point 208°–210° C.

Analysis calculated for $C_{21}H_{28}N_2OS$: C=70.75; H=7.91; N=7.85; S=8.99. Found C=71.02; H=8.08; N=7.93; S=9.08.

EXAMPLE 8

Preparation of
N-[2,6-bis(1-methylethyl)]-N'-[1-(2-thienyl)cyclohexyl]urea

The title compound is prepared according to Example 2. Melting point 170°–171° C.

Analysis calculated for $C_{23}H_{32}N_2OS$: C=71.83; H=8.38; N=7.28; S=8.33. Found C=72.18; H=8.48; N=7.37, S=8.64.

EXAMPLE 9

Preparation of
N-(2,6-diethYlphenYl)-N'-[(1phenylcyclohexyl)methyl]urea

The title compound is prepared according to Example 2. Melting point 185°–186° C.

Analysis is calculated for $C_{24}H_{32}N_2O$: C=79.08; H=8.84; N=7.68. Found C=79.42; H=8.95; N=7.70.

EXAMPLE 10

Preparation of
N-(2,6-dimethylphenyl)-N'-[(1-phenylcYclopentyl)methyl]urea

The title compound is prepared according to Example 2. Melting point 201°–202° C.

Analysis calculated for $C_{21}H_{26}N_2O$: C=78.22; H=8.12; N=8.68. Found C=77.92; H=8.05; N=8.64.

EXAMPLE 11

Preparation of
N-(2,6-dimethylphenyl)-N'-(1-phenylcyclohexyl)methyl]urea

The title compound is prepared according to Example 2. Melting point 207°–208° C.

Analysis calculated for $C_{22}H_{28}N_2O$: C=78.53; H=8.38; N=8.32. Found C=78.59; H=8.37; N=8.46.

EXAMPLE 12

Preparation of
N-(2,6-diethylphenyl)-N'-[(1-phenylcyclopentyl)methyl]urea

The title compound is prepared according to Example 2. Melting point 165°–167° C.

Analysis calculated for $C_{23}H_{30}N_2O$: C=78.62; H=8.62; N=7.99. Found C=78.54; H=8.48; N=7.93.

EXAMPLE 13

Preparation of N-2,6-bis(1-methylethyl)phenyl]-N'-[(1-phenylcyclopentyl)methyl]urea The title compound is prepared according to Example 2. Melting point 181°–183° C.
Analysis calculated for $C_{25}H_{34}N_2O$: C=79.32; H=9.05; N=7.39. Found C=79.01; H=8.97; N=7.21.

EXAMPLE 14

Preparation of N-[2,6-bis(1-methylethyl)phenyl-N'-[(1-phenylcyclohexyl)methyl]urea The title compound is prepared according to Example 2. Melting point 168°–169° C.
Analysis calculated for $C_{26}H_{36}N_2O$: C=79.55; H=9.24; N=7.13. Found C=79.31; H=8.99; N=7.06.

EXAMPLE 15

Preparation of N-[2-methyl-6-(1-methylethyl)phenyl]-N'-[1-(2-thienyl)cyclohexyl]urea The title compound is prepared according to Example 2. Melting point 230°–232° C.
Analysis calculated for $C_{21}H_{28}N_2OS$: C=70.74; H=7.91; N=7.85; S=8.99. Found C=70.53; H=7.88; N=8.03; S=8.90.

EXAMPLE 16

Preparation of N-[2-(1,1-dimethylethyl)-6-methylphenyl]-N'-[1-(2-thienyl)cyclohexyl]urea The title compound is prepared according to Example 2. Melting point 245°–246° C.
Analysis calculated for $C_{22}H_{30}N_2OS$: C=71.31; H=8.16; N=7.55; S=8.65. Found C=71.51; H=8.19; N=7.53; S=8.43.

EXAMPLE 17

Preparation of N-2-methyl-6-(1-methylethyl)phenyl]-N'-[(1-phenylcyclohexyl)methyl]urea The title compound is prepared according to Example 2. Melting point 158°–160° C.
Analysis calculated for $C_{24}H_{32}N_2O$: C=79.08; H=8.84; N=7.68. Found C=78.75; H=8.89; N=7.76.

EXAMPLE 18

Preparation of N-[2-(1,1-dimethylethyl)-6-methylphenyl]-N'-[(1-phenylcyclohexyl)methyl]urea The title compound is prepared according to Example 2. Melting point 196°–197° C.
Analysis calculated for $C_{25}H_{34}N_2O$: C=79.32; H=9.05; N=7.39. Found C=79.11; H=9.27; N=7.36.

EXAMPLE 19

Preparation of N-[2-ethyl-6-(1-methylethyl)phenyl]-N'-[(1-phenylcyclohexyl)methyl]urea The title compound is prepared according to Example 2. Melting point 178°–180° C.
Analysis calculated for $C_{25}H_{34}N_2O$: C=79.32; H=9.05; N=7.39. Found C=79.62; H=9.17; N=7.47.

EXAMPLE 20

Preparation of N-[2-methyl-6-(1-methylethyl)phenyl]-N'-[(1-phenylcyclopentyl)methyl]urea The title compound is prepared according to Example 2. Melting point 157°–159° C.
Analysis calculated for $C_{23}H_{30}N_2O$: C=78.81; H=8.62; N=7.99. Found C=78.48; H=8.61; N=7.93.

EXAMPLE 21

Preparation of N-[2-(1,1-dimethylethyl)-6-methylphenyl]-N'-[1-phenylcyclopentyl)methyl]urea The title compound is prepared according to Example 2. Melting point 196°–197° C.
Analysis calculated for $C_{24}H_{32}N_2O$: C=79.08; H=8.84; N=7.68. Found C=78.65; H=9.01; N=7.58.

EXAMPLE 22

Preparation of N-2-ethyl-6-(1-methylethyl)phenyl]-N'-(1-phenylcyclopentyl)methyl]urea The title compound is prepared according to Example 2. Melting point 152°–154° C.
Analysis calculated for $C_{24}H_{32}N_2O$: C=79.08; H=8.84; N=7.68. Found C=79.17; H=9.05; N=7.65.

EXAMPLE 23

Preparation of N-(2,4-difluorophenyl)-N'-[1-(2-thienyl)cyclohexyl]urea

The title compound is prepared according to Example 1. Melting point 175°–177° C.
Analysis calculated for $C_{17}H_{18}N_2OSF_2$: C=60.70; H=5.39; N=8.32; S=9.53. Found C=60.80; H=5.50; N=8.31; S=9.62.

EXAMPLE 24

Preparation of N-(2,4-difluorophenyl)-N'-[(1-phenylcyclopentyl)methyl]urea

The title compound is prepared according to Example 1. Melting point 160°–161° C.
Analysis calculated for $C_{19}H_{20}N_2OF_2$: C=69.08; H=6.10; N=8.47; F=11.49. Found C=68.94; H=6.09; N=8.32; F=11.55.

EXAMPLE 25

Preparation of N-(2,4-difluorophenyl)-N'-[(1-phenylcyclohexyl)methyl]urea

The title compound is prepared according to Example 1. Melting point 163°–165° C.
Analysis calculated for $C_{20}H_{22}N_2OF_2$: C=69.75; H=6.43; N=8.13; F=11.03. Found C=69.58; H=6.56; N=8.04; F=10.87.

EXAMPLE 26

Preparation of N-(2,6-dibromo-4-fluorophenyl)-N'-(1-phenylcyclohexyl)methyl]urea The title compound is prepared according to Example 2. Melting point 196°–198° C.

Analysis calculated for $C_{20}H_{21}N_2OBr_2F$: C=49.61; H=4.37; N=5.78; Br=33.0; F=3.92. Found C=49.66; H=4.32; N=5.68; Br=32.72; F=3.80.

EXAMPLE 27

Preparation of
N-(2,4-dimethylphenyl)-N'-(1-phenylcyclohexyl)methyl]urea

The title compound is prepared according to Example 2. Melting point 140°–142° C.

Analysis calculated for $C_{22}H_{28}N_2O$: C=78.54; H=8.39; N=8.33. Found C=78.20; H=8.32; N=8.24.

EXAMPLE 28

Preparation of
2-[[[(1-phenylcyclohexyl)methyl]amino]carbonyl]amino]benzoic acid, butyl ester The title compound is prepared according to Example 1. Melting point 83°–85° C.

Analysis calculated for $C_{25}H_{32}N_2O_3$: C=73.50; H=7.90; N=6.86. Found C=73.26; H=7.78; N=6.60.

EXAMPLE 29

Preparation of
N-[2,6-bis(1-methylethyl)phenyl]-N'-[[1-(2-naphthalenyl)cyclobutyl]methyl]urea The title compound is prepared according to Example 1. Melting point 146°–150° C.

Analysis calculated for $C_{28}H_{34}N_2O$: C=81.12; H=8.27; N=6.76. Found C=81.11; H=8.19; N=6.68.

EXAMPLE 30

Preparation of
N-(2,5-dimethylphenyl)-N'-[(1-phenylcyclohexyl)methyl]urea

The title compound is prepared according to Example 2. Melting point 202°–203° C.

Analysis calculated for $C_{22}H_{28}N_2O$: C=78.53; H=8.39; N=8.33. Found C=78.29; H=8.39; N=8.16.

EXAMPLE 31

Preparation of
N-(2,3-dichlorophenyl)-N'-[(1-phenylcyclohexyl)methyl]urea

The title compound is prepared according to Example 2. Melting point 214°–215° C.

Analysis calculated for $C_{20}H_{22}N_2Cl_2O$: C=63.66; H=5.88; N=7.42; Cl=18.79. Found C=63.69; H=5.72; N=7.24; Cl=18.84.

EXAMPLE 32

Preparation of
N-(3,4-dichlorophenyl)-N'-[(1-phenylcyclohexyl)methyl]urea

The title compound is prepared according to Example 2. Melting point 180°–181° C.

Analysis calculated for $C_{20}H_{22}N_2Cl_2O$: C=63.66; H=5.88; N=7.42; Cl=18.79. Found C=63.57; H=5.89; N=7.36; Cl=19.05.

EXAMPLE 33

Preparation of
N-4-(1-methylethyl)phenyl]-N'-(1-phenylcyclohexyl)methyl]urea

The title compound is prepared according to Example 2. Melting point 151°–153° C.

Analysis calculated for $C_{23}H_{30}N_2O$: C=78.82; H=8.63; N=7.99. Found C=78.85; H=8.65; N=7.89.

EXAMPLE 34

Preparation of
N-(4-bromophenyl)-N'-[(1-phenylcyclohexyl)methyl]urea

The title compound is prepared according to Example 2. Melting point 172°–173° C.

Analysis calculated for $C_{20}H_{23}N_2BrO$: C=62.02; H=5.99; N=7.23; Br=20.63. Found C=61.85; H=5.74; N=7.04; Br=20.45.

EXAMPLE 35

Preparation of
N-(4-butoxyphenyl)-N'-[(1-phenylcyclohexyl)methyl]urea

The title compound is prepared according to Example 2. Melting point 142°–143° C.

Analysis calculated for $C_{24}H_{32}N_2O_2$: C=75.75; H=8.48; N=7.36. Found C=75.60; H=8.47; N=7.22.

EXAMPLE 36

Preparation of
N-(4-phenoxyphenyl)-N'-[(1-phenylcyclohexyl)methyl]urea

The title compound is prepared according to Example 2. Melting point 160°–164° C.

Analysis calculated for $C_{26}H_{28}N_2O_2$: C=77.97; H=7.05; N=6.99. Found C=77.87; H=6.92; N=6.98.

EXAMPLE 37

Preparation of
N-(4-nitrophenyl)-N'-[(1-phenylcyclohexyl)methyl]urea

The title compound is prepared according to Example 2. Melting point 240°–241° C.

Analysis calculated for $C_{20}H_{23}N_3O_3$: C=67.97; H=6.56; N=11.67. Found C=67.83; H=6.61; N=11.87.

EXAMPLE 38

Preparation of
N-(4-methoxyphenyl)-N'-[(1-phenylcyclohexyl)methyl]urea.

The title compound is prepared according to Example 2. Melting point 155°–157° C.

Analysis calculated for $C_{21}H_{26}N_2O_2$: C=74.53; H=7.74; N=8.28. Found C=74.16; H=7.66; N=8.19.

EXAMPLE 39

Preparation of
N-(4-ethoxyphenyl)-N'-(1-phenylcyclohexyl)methyl]urea

The title compound is prepared according to Example 2. Melting point 150°–151° C.

Analysis calculated for $C_{22}H_{28}N_2O_2$: C=74.97; H=8.01; N=7.95. Found C=74.96; H=7.94; N=7.79.

EXAMPLE 40

Preparation of
N-(4-acetylphenyl)-N'-[(1-phenylcyclohexyl)methyl-]urea

The title compound is prepared according to Example 2. Melting point 164°–165° C.

Analysis calculated for $C_{22}H_{26}N_2O_2$: C=75.40; H=7.48; N=7.99. Found C=75.31; H=7.42; N=7.78.

EXAMPLE 41

Preparation of
4-[[[(1-phenylcyclohexyl)methyl]amino]carbonyl-]amino]benzoic acid, ethyl ester The title compound is prepared according to Example 1. Melting point 163°–164° C.

Analysis calculated for $C_{23}H_{28}N_2O_3$: C=72.61; H=7.42; N=7.36. Found C=72.64; H=7.49; N=7.29.

EXAMPLE 42

Preparation of
N-(4-methylphenyl)-N'-((1-phenylcyclohexyl)methyl-]urea

The title compound is prepared according to Example 1. Melting point 135°–137° C.

Analysis calculated for $C_{21}H_{26}N_2O$: C=78.22; H=8.13; N=8.69. Found C=78.12; H=8.08; N=8.77.

EXAMPLE 43

Preparation of
N-(4-ethylphenyl)-N'-[(1-phenylcyclohexyl)methyl-]urea

The title compound is prepared according to Example 2. Melting point 138°–139° C.

Analysis calculated for $C_{22}H_{28}N_2O$: C=78.53; H=8.39; N=8.33. Found C=77.93; H=8.22; N=8.23.

EXAMPLE 44

Preparation of
N-(3-methoxyphenyl)-N'-[(1-phenylcyclohexyl)methyl-]urea

The title compound is prepared according to Example 1. Melting point 120°–122° C.

Analysis calculated for $C_{21}H_{26}N_2O_2$: C=74.53; H=7.74; N=8.28. Found C=74.25; H=7.82; N=8.43.

EXAMPLE 45

Preparation of
N-[(1-[1,1'-biphenyl]-4-yl-cyclobutyl)methyl]-N'-[2,6-bis(1-methylethyl)phenyl]urea The title compound is prepared according to Example 2. Melting point 177°–179° C.

Analysis calculated for $C_{30}H_{36}N_2O$: C=81.78; H=8.24; N=6.36. Found C=81.43; H=8.10; N=6.04.

EXAMPLE 46

Preparation of
N-(4-chlorophenyl)-N'-[(1-phenylcyclohexyl)methyl-]urea

The title compound is prepared according to Example 1. Melting point 164°–166° C.

Analysis calculated for $C_{20}H_{23}N_2ClO$: C=70.06; H=6.76; N=8.17; Cl=10.34. Found C=70.08; H=6.67; N=8.01; Cl=10.65.

EXAMPLE 47

Preparation of
N-(4-iodophenyl)-N'-[(1-phenylcyclohexyl)methyl-]urea

The title compound is prepared according to Example 1. Melting range 184°–190° C.

Analysis calculated for $C_{20}H_{23}N_2IO$: C=55.31; H=5.34; N=6.45; I=29.22. Found C=55.12; H=5.29; N=6.24; I=29.47.

EXAMPLE 48

Preparation of
N-(2-methylphenyl)-N'-[(1-phenyl-cyclohexyl)methyl-]urea

The title compound is prepared according to Example 1. Melting point 171°–174° C.

Analysis calculated for $C_{21}H_{26}N_2O$: C=78.22; H=8.13; N=8.69. Found C=78.35; H=8.05; N=8.53.

EXAMPLE 49

Preparation of
N-(3-methylphenyl)-N'-[(1-phenylcyclohexyl)methyl-]urea

The title compound is prepared according to Example 1. Melting point 145°–147° C.

Analysis calculated for $C_{21}H_{26}N_2O$: C=78.22; H=8.13; N=8.69. Found C=78.35; H=7.89; N=8.56.

EXAMPLE 50

Preparation of
N-[2,6-bis(1-methylethyl)phenyl]-N'-[1-[4-(trifluoromethyl)phenyl]cyclobutyl]methyl]urea The title compound is prepared according to Example 1. Melting point 172°–174° C.

Analysis calculated for $C_{25}H_{31}N_2F_3O$: C=69.42; H=7.22; N=6.48; F=13.18. Found C=69.62; H=7.27; N=6.40; F=13.23.

EXAMPLE 51

Preparation of
N-[2,6-bis(1-methylethyl)phenyl]N'-[[1-(4-methylphenyl)cyclobutyl]methyl]urea The title compound is prepared according to Example 1. Melting point 166°–168° C.

Analysis calculated for $C_{25}H_{34}N_2O$: C=79.32; H=9.05; N=7.40. Found C=79.62; H=9.24; N=7.47.

EXAMPLE 52

Preparation of
N-2,6-bis(1-methylethyl)phenyl]-N'-[[1-(2-methylphenyl)cyclobutyl]methyl]urea The title compound is prepared according to Example 1. Melting point 172°–175° C.

Analysis calculated for $C_{25}H_{34}N_2O$: C=79.32; H=9.05; N=7.40. Found C=79.00; H=9.17; N=7.27.

EXAMPLE 53

Preparation of
N-[2,6-bis(1-methylethyl)phenyl]-N'-][1-(1-naphthalenyl)cyclobutyl]methyl]urea The title compound is prepared according to Example 1. Melting point 200°–202° C.

Analysis calculated for $C_{28}H_{34}N_2O$: C=81.12; H=8.27; N=6.76. Found C=79.93; H=8.14; N=6.54.

EXAMPLE 54

Preparation of
N-[2,6-bis(1-methylethyl)phenyl]-N'-[[1-(3-methyl-phenyl)cyclobutyl]methyl]urea The title compound is prepared according to Example 1. Melting point 148°–151° C.

Analysis calculated for $C_{25}H_{34}N_2O$: C=79.32; H=9.05; N=7.40. Found C=79.18; H=8.96; N=7.18.

EXAMPLE 55

Preparation of
N-[(1-phenylcyclohexyl)methyl]-N'-[3-(trifluoromethyl)phenyl]urea The title compound is prepared according to Example 1. Melting point 147°–151° C.

Analysis calculated for $C_{21}H_{23}N_2F_3O$: C=67.01: H=6.16: N=7.44 F=15.14. Found C=67.21: H=6.25; N=7.43: F=14.87.

EXAMPLE 56

Preparation of
N-2-chloro-5-(trifluoromethYl)phenyl]-N'-[(1-phenyl-cyclohexyl)methyl]urea The title compound is prepared according to Example 1. Melting point 188°–190° C.

Analysis calculated for $C_{21}H_{22}N_2ClF_3O$: C=61.39; H=5.40; N=6.82; Cl=8.63; F=13.87. Found C=61.04; H=5.31; N=6.83; Cl=8.46; F=13.97.

EXAMPLE 57

Preparation of
N-(5-chloro-2-methoxyphenyl)-N'-(1-phenylcyclohexyl)methyl]urea

The title compound is prepared according to Example 1. Melting point 180°–181° C.

Analysis calculated for $C_{21}H_{25}N_2ClO_2$: C=67.64; H=6.76; N=7.51; Cl=9.51. Found C=67.30; H=6.75; N=7.41; Cl=9.78.

EXAMPLE 58

Preparation of
N-(4-chloro-2-methylphenyl)-N'-(1-phenylcyclohexyl)-methyl]urea

The title compound is prepared according to Example 1. Melting point 150°–153° C.

Analysis calculated for $C_{21}H_{25}N_2ClO$: C=70.67; H=7.06 N=7.85; Cl=9.93. Found C=70.41; H=6.99; N=7.78; Cl=10.48.

EXAMPLE 59

Preparation of
N-[2,6-bis(1-methylethyl)phenyl]-N'-[[1-(3,4,5-trimethoxyphenyl)cyclobutyl]methyl]urea The title compound is prepared according to Example 1. Melting point 145°–147° C.

Analysis calculated for $C_{27}H_{38}N_2O_4$: C=71.34; H=8.43; N=6.16. Found C=71.61: H=8.59; N=6.15.

EXAMPLE 60

Preparation of
N-[2,6-bis(1-methylethyl)phenyl]-N'-[1-3-(trifluoromethyl)phenyl]cyclobutyl]methyl]urea The title compound is prepared according to Example 1. Melting point 185°–186° C.

Analysis calculated for $C_{25}H_{31}N_2F_3O$: C=69.42; H=7.22; N=6.48; F=13.18. Found C=69.31; H=7.17; N=6.44; F=13.19.

EXAMPLE 61

Preparation of
2-[[[[(1-phenylcyclohexyl)methyl]amino]carbonyl-]amino]benzoic acid, methyl ester The title compound is prepared according to Example 1. Melting range 91°–94° C.

Analysis calculated for $C_{22}H_{26}N_2O_3$: C=72.11; H=7.15; N=7.64. Found C=72.22; H=7.21; N=7.53.

EXAMPLE 62

Preparation of
2-[[[[(1-phenylcyclohexyl)methyl]amino]carbonyl-]amino]benzoic acid, ethyl ester The title compound is prepared according to Example 2. Melting point 99°–101° C.

Analysis calculated for $C_{23}H_{28}N_2O_3$: C=72.61; H=7.42; N=7.36. Found C=72.63; H=7.41; N=7.20.

EXAMPLE 63

Preparation of
N-phenyl-N'-[(1-phenylcyclohexyl)methyl]urea

The title compound is prepared according to Example 1. Melting point 162°–164° C.

Analysis calculated for $C_{20}H_{24}N_2O$: C=77.89; H=7.84; N=9.08. Found C=77.76; H=7.81; N=9.11.

EXAMPLE 64

Preparation of
N-(2,5-dimethoxyphenyl)-N'-[(1phenylcyclohexyl)methyl]urea

The title compound is prepared according to Example 1. Melting point 164°–166° C.

Analysis calculated for $C_{22}H_{28}N_2O_3$: C=71.71; H=7.66; N=7.60. Found C=72.07; H=7.67; N=7.66.

EXAMPLE 65

Preparation of
N-2,6-bis(1-methylethyl)phenyl]-N'-[[1-2-itrifluoromethyl)phenyl]cyclobutyl]methyl]urea The title compound is prepared according to Example 1. Melting point 181°–183° C.

Analysis calculated for $C_{25}H_{31}N_2F_3O$: C=69.42; H=7.22; N=6.48; F=13.18. Found C=69.25; H=7.21; N=6.47; F=13.15.

EXAMPLE 66

Preparation of
N-[2,6-bis(1-methylethyl)phenyl]-N'-[[1-(4-methyl-phenyl)cyclopentyl]methyl]urea The title compound is prepared according to Example 1. Melting point 159°–161° C.

Analysis calculated for $C_{26}H_{36}N_2O$: C=79.55; H=9.24; N=7.14. Found C=79.72; H=9.42; N=7.18.

EXAMPLE 67

Preparation of
N-[2,6-bis(1-methylethyl)phenyl]-N'-[[1-4-(1-methylethyl)phenyl]cyclopentyl]methyl]urea The title compound is prepared according to Example 1. Melting range 133°–141° C.

Analysis calculated for $C_{28}H_{40}N_2O$: C=79.95; H=9.59; N=6.66. [, 20 Found C=79.92; H=9.88; N=6.42.

EXAMPLE 68

Preparation of
N-[2,6-bis(1-methylethyl)phenyl]-N'-[[1-(2-methylphenyl)cyclopentyl]methyl]urea The title compound is prepared according to Example 1. Melting point 147°–150° C.
Analysis calculated for $C_{26}H_{36}N_2O$: C=79.5S; H=9.24; N=7.14. Found C=79.19; H=9.20; N=7.12.

Preparation of
N-[2,6-bis(1-methylethyl)phenyl]-N'-[(1-phenylcyclopropyl)methyl]urea The title compound is prepared according to Example 1. Melting point 138°–142° C.
Analysis calculated for $C_{23}H_{30}N_2O$: C=78.82; H=8.63; N=7.99. Found C=78.87; H=8.65; N=7.98.

EXAMPLE 70

Preparation of
N-(5-chloro-2-methylphenyl)-N'-[(1-phenylcyclohexyl)methyl]urea

The title compound is prepared according to Example 1. Melting point 200°–202° C.
Analysis calculated for $C_{21}H_{25}N_2Cl_2O$: C=70.67; H=7.06; N=7.85; Cl=9.93. Found C=70.58; H=7.06; N=7.74; Cl=9.92.

EXAMPLE 71

Preparation of
N-(2,5-dichlorophenyl)-N'-(1-phenylcyclohexyl)methyl]urea

The title compound is prepared according to Example 1. Melting point 208°–210° C.
Analysis calculated for $C_{20}H_{22}N_2Cl_2O$: C=63.67; H=5.88; N=7.42; Cl=18.79. Found C=63.70; H=5.87; N=7.47; Cl=18.66.

EXAMPLE 72

Preparation of
N-[2,6-bis(1-methylethyl)phenyl]-N'-[[1-(4-methoxyphenyl)cyclopentyl]methyl]urea The title compound is prepared according to Example 1. Melting point 144°–147° C.
Analysis calculated for $C_{26}H_{36}N_2O_2$: C=76.43; H=8.88; N=6.86. Found C=76.60; H=8.91; N=6.78.

EXAMPLE 73

Preparation of
N-2,6-bis(1-methylethyl)phenyl]-N'-[(1-phenylcyclobutyl)methyl]urea The title compound is prepared according to Example 1. Melting point 170°–173° C.
Analysis calculated for $C_{24}H_{32}N_2O$: C=79.08; H=8.85; N=7.68. Found C=79.38; H=8.83; N=7.55.

EXAMPLE 74

Preparation of
N-[2,6-bis(1-methylethyl)phenyl]-N'-[[1-(2-naphthalenyl)cyclopentyl]methyl]urea The title compound is prepared according to Example 1. Melting point 152°–154° C.

Analysis calculated for $C_{29}H_{36}N_2O$: C=81.27; H=8.47; N=6.54. Found C=81.11; H=8.43; N=6.56.

EXAMPLE 75

Preparation of
N-2,6-bis(1-methylethyl)phenyl]-N'-[[1-(2-naphthalenyl)cyclobutyl]methyl]urea The title compound is prepared according to Example 1. Melting range 146°–150° C.
Analysis calculated for $C_{28}H_{34}N_2O$: C=81.12; H=8.27; N=6.76. Found C=81.11; H=8.19; N=6.68.

EXAMPLE 76

Preparation of
N-[2,6-bis(1-methylethyl)phenyl]-N'-[[1-[3-(phenylmethoxy)phenyl]cyclopentyl]methyl]urea The title compound is prepared according to Example 1. Melting point 179°182° C.
Analysis calculated for $C_{32}H_{40}N_2O_2$: C=79.30; H=8.32; N=5.78. Found C=79.22; H=8.35; N=5.71.

EXAMPLE 77

Preparation of
N-[2,6-bis(1-methylethyl)phenyl]-N'-[[1-(4-fluorophenyl)cyclopentyl]methyl]urea The title compound is prepared according to Example 1. Melting point 188°191° C.
Analysis calculated for $C_{25}H_{33}N_2FO$: C=75.72; H=8.39; N=7.06; F=4.79. Found C=75.83; H=8.32; N=7.03; F=4.79.

EXAMPLE 78

Preparation of
N-[2,6-bis(1-methylethyl)phenyl]-N'-[[1-[4-(phenylmethoxy)phenyl]cyclopentyl]methyl]urea The title compound is prepared according to Example 1. Melting point 122°124° C.
Analysis calculated for $C_{32}H_{40}N_2O_2$: C=79.30; H=8.32; N=5.78. Found C=79.41; H=8.31; N=5.56.

EXAMPLE 79

Preparation of
N-[2,6-bis(1-methylethyl)phenyl]-N'-[[1-[4-(trifluoromethyl)phenyl]cyclopentyl]methyl]urea The title compound is prepared according to Example 1. Melting point 196°–197° C.
Analysis calculated for $C_{26}H_{33}N_2F_3O$: C=69.93; H=7.45; N=6.27. Found C=69.96; H=7.52; N=6.41.

EXAMPLE 80

Preparation of
N-[2,6-bis(1-methylethyl)phenyl]-N'-[[1-(2,6-dichlorophenyl)cyclobutyl]methyl]urea The title compound is prepared according to Example 1. Melting point 174°–177° C.
Analysis calculated for $C_{24}H_{30}N_2Cl_2O$: C=66.51; H=6.98; N=6.46. Found C=67.02; H=6.98; N=6.36.

EXAMPLE 81

Preparation of
N-[2,6-bis(1-methylethyl)phenyl]-N'-[[1-[3,5-bis(trifluoromethyl)phenyl]-cyclopentyl]methyl]urea The title compound is prepared according to Example 1. Melting point 165°–168° C.

EXAMPLE 82

Preparation of
N-[2,6-bis(1-methylethyl)phenyl]-N'[[1-2-(trifluoromethyl)phenyl]cyclopentyl]methyl]urea The title compound is prepared according to Example 1. Melting point 156°–159° C.

Analysis calculated for $C_{26}H_{33}N_2F_3O$: C=69.93 H 7.45; N 6.27. Found C=69.69; H=7.50; N=6.11.

EXAMPLE 83

Preparation of
N-[2,6-bis(1-methylethyl)phenyl]-N'-[[1-(4-chlorophenyl)cyclopentyl]methyl]urea The title compound is prepared according to Example 1. Melting point 189°–192° C.

Analysis calculated for $C_{25}H_{33}N_2ClO$: C=72.71; H=8.05; N=6.78. Found C=72.61; H=8.10; N=6.62.

EXAMPLE 84

Preparation of
N-2,6-bis(1-methylethyl)phenyl]-N'-[[1-(4-nitrophenyl)cyclopentyl]methyl]urea The title compound is prepared according to Example 1. Melting point 205°–206° C.

Analysis calculated for $C_{25}H_{33}N_2O_3$: C=70.89; H=7.85; N=9.92. Found C=70.68; H=7.81; N=9.77.

EXAMPLE 85

Preparation of
N'-[[1-(4-aminophenyl)cyclopentylmethyl]-N-[2,6-bis(1-methylethyl)phenyl]urea The nitro compound from Example 84, [5.83 g (0.0127 mol)], was dissolved in 100 mL of methanol and hydrogenated using 2 g of Raney nickel as catalyst. After removal of the catalyst, the methanol solution was concentrated under vacuum and the residual white solid was recrystallized from methanol to yield the title compound. Melting point 178°–179° C.

Analysis calculated for $C_{25}H_{35}N_3O$: C=76.29; H=8.96; N=10.68. Found C=76.32; H=8.92; N=10.66.

EXAMPLE 86

Preparation of
N-[4-[1-[[[[2,6-bis(1-methylethyl)phenyl]amino]carbonyl]amino]methyl]cyclopentyl]phenyl]acetamide The amino compound from Example 85, [3.7 g (0.0009 mol)], was dissolved in 30 mL of tetrahydrofuran containing 0.95 g (0.009 mol) of triethylamine. To this solution was added, with stirring, 0.74 g (0.009 mol) of acetyl chloride dissolved in 20 mL of tetrahydrofuran. The resulting mixture was stirred overnight and the white solid product was collected by filtration and suspended in water. The insoluble material was collected by filtration, washed with cold water, and dried in vacuo to yield the title compound. Melting point 265°–266° C.

Analysis calculated for $C_{27}H_{37}N_3O_2$: C=74.45; H=8.56; N=9.65. Found C=74.34; H=8.93; N=9.40.

EXAMPLE 87

Preparation of
N-[2,6-bis(1-methylethyl)phenyl]-N'-[[1-(4-dimethylaminophenyl)cyclopentyl]methyl]urea The title compound was prepared according to Example 1. Melting point 132°–133° C.

Analysis calculated for $C_{27}H_{39}N_3O$: C=76.92; H=9.32; N=9.97. Found C=77.00; H=9.37; N=9.91. The starting [1-(4-dimethylaminophenyl)cyclopentyl]methylamine was prepared as follows:

1-Cyano-1-(4-nitrophenyl)cyclopentane

To 79.2 g (1.65 m) of 50% sodium hydride suspended in 750 ml DMSO was added dropwise a mixture of 121.6 g (0.75 mole) p-nitrophenylacetonitrile and 161.7 ml (0.75 mole) 1,4 dibromobutane in 750 ml of a 50:50 mixture of DMSO, diethyl ether. The temperature was held between 25°–30° C. The reaction mixture was stirred at room temperature overnight then cooled to 10° C. Thirty-eight ml of isopropanol was added followed by the cautious addition of 2.8 l of water. Air was bubbled through the black reaction mixture to remove most of the ether. Black solid was filtered and taken up in diethyl ether. The ether solution was washed two times with 2 N HCl and two times with brine, dried over MgSO$_4$, and concentrated in vacuo. The resulting dark solid was extracted six times with boiling hexane. The hexane solution was concentrated to a small volume to yield 127.5 g of product, melting point 76°–77° C.

1-Cyano-1-(4-dimethylaminophenyl)cyclopentane

In a pressure reactor was placed 127.5 g (0.59 mole) of 1-cyano-1-(4-nitrophenyl)cyclopentane and 1600 ml of methanol. One gram of 10% Pd/C was added to the reactor and charged with hydrogen. The reaction mixture was shaken at room temperature until the theoretical amount of hydrogen had been taken up. The reactor was vented and 100.5 g of 37% formaldehyde and 5 g of 10% Pd/C was added and shaken at room temperature for 16 hours. The reaction mixture was filtered and the filtrate concentrated in vacuo to give a sticky solid. The solid was taken up in ether and washed two times with a sodium bisulfite solution and two times with brine, dried over MgSO$_4$, and concentrated in vacuo. The product was purified by chromatography, using a gradient of 90% hexane: 10% ethylacetate to 70% hexane: 30% ethylacetate as eluant. There was obtained 94 g of the title compound, melting point 73°–74° C.

Analysis calculated for $C_{14}H_{18}N_2$: C=78.46; H=8.47; N=13.07. Found C=78.48; H=8.50; N=13.03.

[1-(4-dimethylaminophenyl)cyclopentyl]methylamine

In a pressure reactor was placed 281.2 g (1.3 mole) of 1-cyano-1-(4-dimethylaminophenyl)cyclopentane, 3500 ml of methanol, 600 g of anhydrous ammonia, and 200 g of Raney nickel. Hydrogen was charged into the stirred reaction vessel. The reaction was stirred at room temperature until the theoretical amount of hydrogen had been taken up. The reaction mixture was filtered and the filtrate concentrated in vacuo to yield 284.4 g of the title compound, melting point 87°–89° C.

Analysis calculated for $C_{14}H_{22}N_2$: C=77.01; H=10.16; N=12.83. Found C=76.81; H=10.13; N=12.63.

---

Analysis calculated for $C_{27}H_{32}N_2F_6O$: C=63.03 H=6.27: N=5.44. Found C=63.08; H=6.31: N=5.32.

EXAMPLE 88

Preparation of
N-[2,6-bis(1-methylethyl)phenyl]-N'-[[1-[4-(dimethylamino)phenyl]cyclopentyl]methyl]urea; Hydrochloride To 40 g (0.045 m) of the free base from Example 87 in 350 ml toluene was added, with stirring 8.13 ml (0.095 m) concentrated hydrochloric acid. A gummy solid separated. The reaction mixture was heated to boiling and the water allowed to azeatrope off. The reaction mixture was cooled and the white solid filtered. The solid was washed well with acetone and ether and dried in vacuo at 60° to yield 45.4 g of the title compound, melting point 230°–231° C. dec.

Analysis calculated for $C_{27}H_{39}N_3O \cdot HCl$: C=70.79; H=8.80; N=9.17; Cl=7.74. Found C=70.79; H=8.97; N=9.08; Cl=7.83.

EXAMPLE 89

Preparation of
N-[2,6-bis(1-methylethyl)phenyl]-N'-[[1-[4-(dimethylamino)phenyl]cyclohexyl]methyl]Urea Using the same method as in Example 87 but substituting p-dimethylaminophenyl-1-cyclohexane methyl amine for p-dimethylaminophenyl-1-cyclopentane methyl amine was obtained 7.0 g of the title compound that was purified by chromatography using a 50:50 mixture of ethylacetate:hexane as eluant.

Analysis calculated for $C_{28}H_{41}N_3O \cdot 0.25\ H_2O$: C=76.40; H=9.50; N=9.54. Found C=76.38; H=9.45; N=9.28.

EXAMPLE 90

Preparation of
N-[2,6-bis(1-methylethyl)phenyl]-N'-[[1-[4-(diethylamino)phenyl]cyclopentyl]methyl]urea The title compound was prepared according to Example 2. Melting point 138°–140° C.

Analysis calculated for $C_{29}H_{43}N_3O$: C=77.46: H=9.64: N=9.34. Found C=77.57 H=9.69 N=9.18.

The starting [1-(4-diethylaminophenyl)cyclopentyl]methylamine was prepared as follows:

1-Cyano-1-(4-diethylaminophenyl)cyclopentane

In a pressure reactor was placed 43.4 g (0.2 mole) of 1-cyano-1-(4-nitrophenyl)cyclopentane and 500 mL of absolute ethanol. One gram of 5% Pd/C was added, the reactor charged with hydrogen and shaken at room temperature until the theoretical amount of hydrogen had been taken up. The reactor was vented and 22 g (0.5 mole) of acetaldehyde and 2 g of 10% Pd/C was added. The reactor was charged with hydrogen and shaken at room temperature for 16 hours. The reaction mixture was then filtered and the filtrate concentrated in vacuo. The product was purified by chromatography, using a gradient of 90% hexane: 10% ethylacetate to 70% hexane: 30% ethylacetate as eluant. There was obtained 10.7 g of a clear oil.

[1-(4-diethylaminophenyl)cyclopentyl]methylamine

In a pressure reactor was placed 10.4 g (0.043 mole) of 1-cyano-1-(4-diethylaminophenyl)cyclopentane, 100 mL of methanolic ammonia, and 10 g of Ra-Ni catalyst. The reactor was charged with hydrogen and shaken at room temperature until the theoretical amount of hydrogen was taken up. The reaction mixture was filtered and the filtrate concentrated in vacuo to yield 9.9 g of the desired amine.

EXAMPLES 91 AND 92

Preparation of N-[2,6 bis(1-methylethyl)phenyl]-N'-[[1-[4-[(2-hydroxyethyl)amino]phenyl]cyclopentyl]methyl and N'-[[1-[4-[-bis(2-hydroxyethyl)amino]phenyl]cyclopentyl]methyl]-N-[2,6-bis(1-methylethyl)phenyl]urea Ethylene oxide was bubbled into a solution of 2.93 g (0.01 mole) of compound 85 in 10 cc methanol. After 15 minutes the ethylene oxide was stopped and the solution stirred at reflux for three hours. Ethylene oxide was again bubbled into the reaction mixture for 15 minutes then it was stirred at reflux overnight. The reaction mixture was concentrated in vacuo. The residue was taken up in a mixture of 90% ethylacetate: 10% hexane and the two products separated on a column of silica gel. The monoalkylated product (Example 91) had an Rf of 0.24, yield 900 mg, melting point 159°–161° C.

Analysis calculated for $C_{27}H_{39}N_3O_2 \cdot 0.5H_2O$: C=72.60; H=9.02; N=9.40 Found C=72.44; H=8.83; N=9.03.

The dialkylated product (Example 92) had an Rf of 0.5, yield 1.6 g, mp 139°–141° C.

Analysis calculated for $C_{29}H_{43}N_3O_3$: C=72.31; H=8.99; N=8.72. Found C=72.28; H=8.82; N=8.66.

EXAMPLE 93

Preparation of
N-[2,6-bis(1-methylethyl)phenyl]-N'-[[1-(2-trifluoromethyl-4-dimethylamino)phenylcyclopentyl]methyl]urea The title compound was prepared by dissolving [1-(2-trifluoromethyl-4-dimethylamino)phenylcyclopentyl]-methylamine (1.7 g, 0.006 mol) and [2,6-bis(1methylethyl)phenylisocyanate (1.2 g, 0.006 mol) together in 100 mL of ethyl acetate. The reaction mixture was stirred at room temperature for 20 hours. Volatiles were removed under reduced pressure and the residue was purified by flash column chromatography, eluting with 20% ethyl acetate/hexane. The desired product (Rf=0.15 in 20% ethyl acetate/hexane) was isolated as 3.1 g of a shiny white solid, melting point 74°–78° C.

Analysis calculated for $C_{28}H_{38}F_3N_3O$: C=68.69; H=7.82; N=8.58; F=11.64. Found C=68.81; H=7.87; N=8.18; F=11.28.

EXAMPLE 94

N-2,6-bis(1-methylethyl)phenyl)-N'-[[[1-(2-trifluoromethyl-4-methylamino)phenylcyclopentyl]methyl]urea The title compound was prepared in a similar manner as Example 93. 1.9 g of a fluffy white solid (Rf=0.20 in 20% ethyl acetate/hexane) was isolated, melting point 66°–71° C.

Analysis calculated for $C_{27}H_{36}F_3N_3O$: C=68.19; H=7.63; N=8.84; F=11.98. Found C=68.10; H=7.63; N=8.18; F=11.27.

The requisite amines were prepared as follows:

1-Cyano-1-(2-trifluoromethyl-4-nitro)phenyl cyclopentane

To 200 mL of fuming nitric acid at 5° C. was added cautiously 20.0 g (0.084 mol) of 1-cyano-1-(2-trifluoromethyl)phenylcyclopentane. The mixture was stirred at 5° C. for one hour, then at room temperature for an additional two hours. The reaction mixture was then poured into 2 L of ice water; the acidic solution was extracted with 3×500 mL diethyl ether. The organic extracts were washed with 500 mL of water; followed by 2×500 mL saturated NaHCO$_3$ (cautiously); and 500 mL water. The organic solution was dried over MgSO$_4$, filtered, and concentrated under vacuum. The crude oil was purified by flash column chromatography on a silica gel column, eluting gradiently with 10% ethyl acetate/hexane to 30% ethyl acetate/hexane. 12.9 g of semi-solid thus obtained was suspended in hexane and the white solid was collected to afford 9.3 g of the desired nitrile, (Rf=0.43 in 20% ethyl acetate/hexane) melting point 83°–89° C.

Analysis calculated for $C_{13}H_{11}F_3N_2O_2$: C=54.93; H=3.90; N=9.86; F=20.05. Found C=54.95; H=3.89; N=9.87; F=19.34.

1-Cyano-1-(2-trifluoromethyl-4-dimethylamino)phenyl-cyclopentane and
1-cyano-1-(2-trifluoromethyl-4-methylamino)phenylcyclopentane In a pressure reactor were placed 9.03 g (0.032 mol) of 1-cyano-1-(2-trifluoromethyl-4-nitro)phenylcyclopentane, 100 mL of methanol, and 0.25 g of 10% Pd/C. The reactor was charged with hydrogen and shaken at room temperature until the theoretical amount of hydrogen had been consumed. The reactor was vented and 5.41 g of 37% formaldehyde and 1.0 g of 10% Pd/C were added and shaken at room temperature for 24 hours. The reaction mixture was filtered and the filtrate was concentrated under vacuum. The residue was taken up in 500 mL chloroform and washed with 2×250 mL dilute Na$_2$SO$_3$, then with 250 mL brine. The solution was dried over Na$_2$SO$_4$, filtered, and concentrated to give a crude oil. The products were isolated by flash column chromatography on silica gel, eluting gradiently with 5% ethyl acetate/hexane to 20% ethyl acetate/hexane.

The first title compound was isolated as 2.1 g of a white crystalline solid, (Rf=0.43 in 20% ethyl acetate/hexane).

The second title compound was isolated as 1.73 g of a yellow oil (Rf=0.27 in 20% ethyl acetate/hexane).

[[1-(2-trifluoromethyl-4-dimethylamino)phenyl]cyclopentyl]methylamine

In a pressure reactor were placed 1.92 g (0.007 mol) of 1-cyano-1-(2-trifluoromethyl-4-dimethylamino)phenyl cyclopentane, 100 mL of ammonia-saturated methanol, and 1.0 g of Raney Ni. The vessel was charged with hydrogen and shaken at room temperature until the theoretical amount of hydrogen had been taken up. The reaction mixture was filtered and the filtrate was concentrated in vacuo to afford 1.7 g of the title compound—as an oil.

[[1-(2-trifluoromethyl-4-methylamino)phenyl]cyclopentyl]methylamine

The amine was prepared in the same manner as described above yielding 1.65 g of the desired amine.

EXAMPLE 95

Preparation of
N-(2,6-bis(1-methylethyl)phenyl)-N'-[[1-(5-(2-methyl-2H-tetrazolyl))-cyclopentyl]methyl]urea 2,6-Bis(1-methylethyl)phenyl isocyanate (2.37 mL) was added dropwise to a stirred solution of 1-(2-methyl-5-tetrazolyl)cyclopentyl amine (2 g, 11 mmoles) in 15 mL of methylene chloride at room temperature. After the exothermic reaction subsided, the solution was concentrated and the resulting solid recrystallized from ethyl acetate to afford 2.43 g of a colorless solid. Melting point 143°–145° C.

Analysis calculated for $C_{21}H_{32}N_6O$: C=65.60; H=8.39; N=21.87. Found C=65.61; H=8.48; N=21.96.

The 1-(2-methyl-5-tetrazolyl)cyclopentylamine was prepared as follows:

1-Cyano-1-(5-tetrazolyl)cyclopentane

A mixture of 1,1-biscyanocyclopentane (58 g), sodium azide (29.9 g, 460 mmoles) and ammonium chloride (28.5 g, 531 mmoles) in DMF (500 mL) was stirred and heated at 130° C. for 90 minutes. The cooled mixture was poured into 0.5 M HCl (1 liter) and extracted with ether (2×500 mL). The combined ether extracts were washed with water (2×200 mL), brine (100 mL), and dried (MgSO$_4$). Filtration and concentration provided a solid which was recrystallized from isopropylether-hexane (16.8 g). Melting point 92°–94° C.

Analysis calculated for $C_7H_9N_5$: C=51.52; H=5.56; N=42.92. Found C=57.80; H=5.62; N=43.41.

1-Cyano-[5-(2-methyl)tetrazolyl]cyclopentane

A solution of 1-cyano-1-(5-tetrazolyl)cyclopentane (4.0 g, 245 mmoles) in DMF (20 mL) was added dropwise to a room temperature suspension of hexane-washed NaH (27 mmoles) in 10 mL of DMF. When gas evolution had subsided, CH$_3$I (1.59 mL, 25.5 mmoles) was added dropwise. The solution was stirred overnight at room temperature, diluted with H$_2$O (100 mL), and extracted with ether (2×200 mL). The combined ether extracts were washed with H$_2$O (2×50 mL), brine (50 mL), and dried (MgSO$_4$). The oil remaining after filtration and concentration was chromatographed.

Isolated 2.9 g (R$_f$≅0.2 3:1 hex-EtOAc), 250 MHz. NMR (CDCl$_3$) δ 2.0 (m, 4H), 2.55 (m, 4H), 4.37 (s, 3H).

Analysis calculated for $C_8H_{11}N_5$: C=54.22; H=6.25; N=39.52. Found C=54.21; H=6.19; N=39.14.

1-(2-Methy-5-tetrazolyl)cyclopentylamine 4.07 g (23 mmoles) of 1-cyano-1-[5-(2-methyl)tetrazolyl]cyclopentane was dissolved in 100 mL of CH$_3$OH/NH$_3$ and shaken with 3 g of Ra-Ni (washed Raney Nickel) under H$_2$ until two equivalents (H$_2$) were taken up. It was then filtered and concentrated to provide 3.8 g of a greenish liquid which had a 90 MHz NMR consistent with the expected product. It was used without further purification. 90 MHz NMR (CDCl$_3$) δ1.8 (m, 4H), 2.2 (m, 4H); 3.0 (m, 2H), 4.30 (s, 3H).

We claim:

1. A compound having the formula

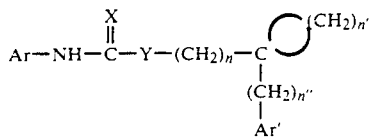

wherein Ar is
 phenyl;
 naphthyl;
 phenyl substituted with
  alkyl of from one to six carbon atoms,
  alkoxy of from one to six carbon atoms,
  phenoxy,
  hydroxy,
  fluorine,
  chlorine,
  bromine,
  nitro,
  trifluoromethyl,
  —COOH,
  —COO-alkyl (where alkyl is from one to four carbon atoms), or
  —NR₁R₂ wherein
   R₁ and R₂ are independently hydrogen, or alkyl of from one to six carbon atoms;
 naphthyl substituted with
  alkyl of from one to six carbon atoms,
  alkoxy of from one to six carbon atoms,
  hydroxy,
  fluorine,
  chlorine,
  bromine,
  nitro,
  trifluoromethyl,
  —COOH,
  —COO-alkyl (where alkyl is from one to four carbon atoms), or
  —NR₁R₂ wherein
   R₁ and R₂ are independently hydrogen, or alkyl of from one to six carbon atoms;
X is oxygen or sulfur;
Y is —NH—;
n is zero or is an integer of from one to three;
n′ is an integer of from two to six; and
n″ is zero, one, or two;
Ar′ is
 phenyl,
 naphthyl, or a 5- or 6-membered monocyclic or fused bicyclic heterocycle containing at least one to four nitrogen, oxygen or sulfur atoms in at least one ring member;
 phenyl, naphthyl or said heterocycle substituted with
  alkyl of from one to six carbon atoms,
  alkoxy of from one to six carbon atoms,
  hydroxy,
  benzyloxy,
  fluorine,
  chlorine,
  bromine,
  nitro,
  trifluoromethyl,
  —NH—COCH₃,
  —CONH₂,
  —COOH,
  —CH₂COOH,
  —CH₂CONH₂,
  —NR₁R₂ wherein
   R₁ and R₂ are independently hydrogen, alkyl of from one to six carbon atoms which terminal carbon may contain an OR₃ group where R₃ is hydrogen, alkyl of from one to six carbon atoms, alkanoyl having from 2 to 5 carbon atoms, benzoyl, or when joined together form a 5- or 6-membered ring optionally interrupted by an oxygen atom or —NR₃′; wherein R₃ is as defined above;
  —CH₂NR₁R₂ where R₁ and R₂ are as defined above;
  —CH₂OR₃ where R₃ is as defined above;
  —COO-alkyl where alkyl is from one to six carbons which terminal carbon may contain an OR₃ group or NR₁R₂ where R₁, R₂, and R₃ are as defined above;
  —NHCH₂COO-alkyl where alkyl is from one to four carbon atoms;
  —SO₂NR₁R₂ where R₁ and R₂ are as defined above;
  —SO₂OR₃ where R₃ is as defined above, or
  —NH—SO₂R₄ where R₄ is alkyl of one to four carbon atoms or phenyl;
 a N-oxide or
a pharmaceutically acceptable salt thereof.

2. A compound as defined by claim 1 wherein X is oxygen.

3. A compound as defined by claim 1 wherein Ar′ is phenyl or phenyl substituted by
 alkyl of from one to six carbon atoms;
 hydroxy;
 alkoxy of from one to six carbon atoms;
 benzyloxy;
 fluorine;
 chlorine;
 bromine;
 nitro;
 trifluoromethyl;
 —NH—COCH₃;
 —CONH₂;
 —COOH;
 —CH₂COOH;
 —CH₂CONH₂;
 —NR₁R₂ in which R₁ and R₂ are independently hydrogen, alkyl of from one to six carbon atoms which terminal carbon may contain an OR₃ group where R₃ is hydrogen, alkyl of from one to six carbon atoms, alkanoyl of from two to five carbon atoms, benzoyl, or when joined together form a 5- or 6-membered ring optionally interrupted by an oxygen atom or —NR₃ wherein R₃ is as defined above;
 —CH₂NR₁R₂ where R₁ and R₂ are as defined above;
 —CH₂OR₂ where R₃ is as defined above;
 —COO-alkyl where alkyl is from one to six carbons which terminal carbon may contain an OR₃ group or NR₁R₂ where R₁, R₂, and R₃ are as defined above;
 —NHCH₂COO-alkyl where alkyl is from one to four carbon atoms;
 —SO₂NR₁R₂ where R₁ and R₂ are as defined above;
 —SO₂OR₃ where R₃ is as defined above, or
 —NH—SO₂R₄ where R₄ is alkyl of one to four carbon atoms or phenyl.

4. A compound as defined by claim 1 wherein Ar′ is phenyl or phenyl substituted by alkyl of from one to six carbon atoms,
alkoxy of from one to six carbon atoms,
hydroxy,
fluorine,
chlorine,
bromine,
nitro,
trifluoromethyl,
—COOH,
—COO-alkyl where akyl is from one to four carbon atoms, or
—NR$_1$R$_2$ wherein
R$_1$ and R$_2$ are independently hydrogen, or
alkyl of from one to six carbon atoms.

5. A compound of formula

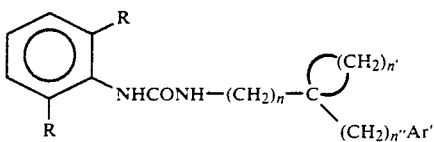

wherein R is alkyl of one to four carbon atoms;
n is zero or 1;
n' is an integer from 2 to 6;
n'' is zero or 1, and
Ar' is phenyl or phenyl substituted by
alkyl of from one to six carbon atoms;
hydroxy;
alkoxy of from one to six carbon atoms;
benzyloxy;
fluorine;
chlorine;
bromine;
nitro;
trifluoromethyl;
—NH—COCH$_3$;
—CONH$_2$;
—COOH;
—CH$_2$COOH;
—CH$_2$CONH$_2$;
—NR$_1$R$_2$ in which R$_1$ and R$_2$ are independently hydrogen, alkyl of from one to six carbon atoms which terminal carbon may contain an OR$_3$ group where R$_3$ is hydrogen or alkyl of from one to six carbon atoms, or when joined together form a 5- or 6-membered ring optionally interrupted by an oxygen atom or —NR$_3$';
—CH$_2$NR$_1$R$_2$ where R$_1$ and R$_2$ are as defined above;
—CH$_2$OR$_3$ where R$_3$ is as defined above;
—COO-alkyl where alkyl is from one to six carbons which terminal carbon may contain an OR$_3$ group or NR$_1$R$_2$ where R$_1$, R$_2$, and R$_3$ are as defined above;
—NHCH$_2$COO-alkyl (where alkyl is from one to four carbon atoms);
—SO$_2$NR$_1$R$_2$ where R$_1$ and R$_2$ are as defined above;
—SO$_2$OR$_3$ where R$_3$ is as defined above, or
—NH—SO$_2$R$_4$ where R$_4$ is alkyl of one to four carbon atoms or phenyl.

6. A compound as defined by claim 5 wherein Ar' is phenyl or phenyl substituted by
alkyl of from one to six carbon atoms,
alkoxy of from one to six carbon atoms,
hydroxy,
fluorine,
chlorine,
bromine,
nitro,
trifluoromethyl,
—COOH,
—COO-alkyl (where alkyl is from one to four carbon atoms), or
—NR$_1$R$_2$ wherein
R$_1$ and R$_2$ are independently hydrogen, or
alkyl of from one to six carbon atoms.

7. A compound as defined by claim 1 and of the formula

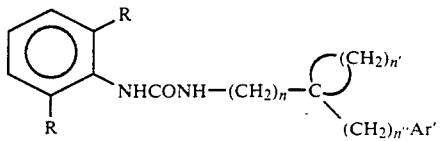

wherein R is lower alkyl;
n is zero or 1;
n' is an integer from 2 to 6;
n'' is zero or 1, and
Ar' is thienyl,
furanyl,
idyl,
benzothienyl,
benzofuranyl,
pyrimidinyl,
pyridazinyl,
pyrazinyl,
pyrrolyl,
pyrrazolyl,
isothiazolyl,
oxazolyl,
isoxazolyl,
triazolyl,
tetrazolyl,
imidazolyl,
benzothiazolyl,
indolyl,
quinolinyl,
isoquinolinyl, or
Ar' substituted by
alkyl of from one to six carbon atoms,
alkoxy of from one to six carbon atoms,
hydroxy,
fluorine,
chlorine,
bromine,
nitro,
trifluoromethyl,
—NH—COCH$_3$,
—CONH$_2$,
—COOH,
—COO-alkyl where alkyl is from one to four carbon atoms,
—CH$_2$COOH,
—CH$_2$CONH$_2$, or
—NR$_1$R$_2$ wherein
R$_1$ and R$_2$ are independently hydrogen or
alkyl of from one to six carbon atoms.

8. A compound as defined by claim 1 wherein n' is 2.

9. A compound as defined by claim 8 selected from the group consisting of

N-(2,6-diethylphenyl)—N'-[(1-phenylcyclopropyl)methyl]urea; and
N-[2,6-bis(1-methylethyl)phenyl]—N'-[(1-phenylcyclopropyl)methyl]urea.

10. A compound as defined by claim 1 wherein n' is 3.

11. A compound as defined by claim 10 selected from the group consisting of
N-(2,6-diethylphenyl)—N'-(1-phenylcyclobutyl)urea;
N-[2,6-bis(1-methylethyl)phenyl]—N'-[(1-phenylcyclobutyl)methyl]urea;
N-[2,6-bis(1-methylethyl)phenyl]—N'-[[1-(2-methylphenyl)cyclobutylmethyl]urea;
N-[2,6bis(1-methylethyl)phenyl]-N'-[[1-(3methylphenyl)cyclobutyl]methyl]urea; and
N-[2,6-bis(1-methylethyl)phenyl]—N'-[[1-(4-methylphenyl)cyclobutyl]methyl]urea.

12. A compound as defined by claim 7 selected from the group consisting of
N-[2,6-bis(1-methylethyl)phenyl]—N'-[[1-(1-naphthalenyl)cyclobutyl]methyl]urea;
N-[2,6-bis(1-methylethyl)phenyl]—N'-[1-(2-naphthalenyl)cyclobutyl]methyl]urea; and
N-[2,6-bis(1-methylethyl)phenyl]—N'-[[1-(2-naphthalenyl)cyclobutyl]methyl]urea.

13. A compound as defined by claim 10 selected from the group consisting of
N-[2,6bis(1-methylethyl)phenyl]—N'-[[1-(2,6-dichlorophenyl)cyclobutyl]methyl]urea.

14. A compound as defined by claim 10 selected from the group consisting of
N-[2,6-bis(1-methylethyl)phenyl]—N'-[[1-(3,4,5-trimethoxyphenyl)cyclobutyl]methyl]urea;
N-[2,6-bis(1-methylethyl)phenyl]—N'-[[1-2-(trifluoromethyl)phenyl]cyclobutyl]methyl]urea;
N-[2,6-bis(1-methylethyl)phenyl]—N'-[[1-[3-(trifluoromethyl)phenyl]cyclobutyl]methyl]urea
N-[2,6-bis(1-methylethyl)phenyl]—N'-[[1-[4-(trifluoromethyl)phenyl]cyclobutyl]methyl]urea;

15. A compound as defined by claim 1 wherein n' is 4.

16. A compound as defined by claim 15 selected from the group consisting of
N-(2,6-dimethylphenyl)—N'-(1-phenylcyclopentyl)urea;
N-(2,6-diethylphenyl)—N'-(1-phenylcyclopentyl)urea;
N-(2,6-dimethylphenyl)—N'-[(1-phenylcyclopentyl)methyl]urea;
N-(2,6-diethylphenyl)—N'-[(1-phenylcyclopentyl)methyl]urea;
N-[2,6-bis(1-methylethyl)phenyl]-N'-[(1-phenylcyclopentyl)methyl]urea;
N-[2-methyl-6-(1-methylethyl)phenyl]-N'-[(1-phenylcyclopentyl)methyl]urea;
N-[2-(1,1-dimethylethyl)-6-methylphenyl]-N'-[(1-phenylcyclopentyl)methyl]urea;
N-[2-ethyl-6-(1-methylethyl)phenyl]-N'-[(1-phenylcyclopentyl)methyl]urea;
N-[2,6-bis(1-methylethyl)phenyl]-N'-[[1-(4-methylphenyl)cyclopentyl]methyl]urea;
N-[2,6-bis(1-methylethyl)phenyl]-N'-[[1-[4-(1-methylethyl)phenyl]cyclopentyl]methyl]urea;
N-[2,6-bis(1-methylethyl)phenyl]-N'-[[1-(2-methylphenyl)cyclopentyl]methyl]urea; and
N-[2,6-bis(1-methylethyl)phenyl]-N'-[[1-(2naphthalenyl)cyclopentyl]methyl]urea.

17. A compound as defined by claim 15 selected from the group consisting of
N-[2,6-bis(1-methylethyl)phenyl]-N'-[[1-(4-fluorophenyl)cyclopentyl]methyl]urea;
N-(2,4-difluorophenyl)-N'-[(1-phenylcyclopentyl)methyl]urea; and
N-[2,6-bis(1-methylethyl)phenyl]-N'-[[1-(4-chlorophenyl)cyclopentyl]methyl]urea.

18. A compound as defined by claim 15 selected from the group consisting of
N-[2,6-bis(1-methylethyl)phenyl]-N'-[[1-(4-methoxyphenyl)cyclopentyl]methyl]urea;
N-[2,6-bis(1-methylethyl)phenyl]-N'-[[1-[3-(phenylmethoxy)phenyl]cyclopentyl]methyl]urea;
N-[2,6-bis(1-methylethyl)phenyl]-N'-[[1-[4-(phenylmethoxy)phenyl]cyclopentyl]methyl]urea;
N-(1-phenylcyclopentyl)-N'-(2,4,6-trimethoxyphenyl)urea;
N-[2,6-bis(1-methylethyl)phenyl]-N'-[[1-[2-(trifluoromethyl)phenyl]cyclopentyl]-methyl]urea;
N-(2,6bis-(1-methylethyl)phenyl]-N'-[[1-[4-(trifluoromethyl)phenyl]cyclopentyl]-methyl]urea;
N-[2,6-bis(1-methylethyl)phenyl]-N'-[[1-[3,5-bis(trifluoromethyl)phenyl]cyclopentyl]methylurea;
N-[2,6-bis(1-methylethyl)phenyl]-N'-[[1-(4-nitrophenyl)cyclopentyl]methyl]urea;
N-[[1-(4-aminophenyl)cyclopentyl]methyl]-N,-[2,6-bis(1-methylethyl)phenyl]urea; and
N-[4-[1-[[[[[2,6-bis(1-methylethyl)phenylamino]carbonyl]amino]methyl]cyclopentyl]phenyl]acetamide.

19. A compound as defined by claim 15 and being N-[2,6-bis(1-methylethyl)phenyl]-N'-[[1-(4-dimethylaminophenyl)cyclopentyl]methyl]urea.

20. A compound as defined by claim 16 selected from the group consisting of:
N-[2,6-bis(1-methylethyl)phenyl]-N'-[[1-(4-diethylaminophenyl)cyclopentylmethyl]urea;
N-[2,6-bis(1-methylethyl)phenyl]-N'-[[[1-[4-(2-hydroxyethyl)amino]phenyl]cyclopentyl]methyl]urea;
N'-[[1-[4-[bis(2-hydroxyethyl)amino]phenyl]cyclopentyl]methyl]—
N-[2,6-bis(1-methylethyl)phenyl]urea;
N-[2,6-bis(1-methylethyl)phenyl]-N'-[[[1-(2pentyl]methyl]urea; and
N-[2,6-bis(1-methylethyl)phenyl]-N'-[[[1-(2-trifluoromethyl-4-methylamino)phenyl]cyclopentyl]methyl]urea.

21. A compound as defined by claim 1 wherein n' is 5.

22. A compound as defined by claim 21 selected from the group consisting of
N-(2,6-dimethylphenyl)-N'-[(1-phenylcyclohexyl)methyl]urea;
N-(2,6-diethylphenyl)-N'-[(1-phenylcyclohexyl)methyl]urea;
N-[2,6-bis(1-methylethyl)phenyl]-N'-[(1-phenylcyclohexyl)methyl]urea;
N-[2,6-bis(1-methylethyl)phenyl]-N'-[[1-(4-dimethylaminophenyl)cyclohexyl]methyl]urea;
N-[2-methyl-6-(1-methylethyl)phenyl]-N'-[(1-phenylcyclohexyl)methyl]urea;
N-[2-ethyl-6-(1-methylethyl)phenyl]-N'-[(1-phenylcyclohexyl)methyl]urea;
N-[2-(1,1-dimethylethyl)-6-methylphenyl]-N'-[(1-phenylcyclohexyl)methyl]urea;
N-phenyl-N'-[(1-phenylcyclohexyl)methyl]urea;
N-(2-methylphenyl)-N'-[(1-phenylcyclohexyl)methyl]urea;
N-(3-methylphenyl)-N'-[(1-phenylcyclohexyl)methyl]urea;
N-(4-ethylphenyl)-N'-[(1-phenylcyclohexyl)methyl]urea;

N-(4-methylphenyl)-N'-[(1-phenylcyclohexyl)methyl]urea;

N-[4-(1-methylethyl)phenyl]-N'-[(1-phenylcyclohexyl)methyl]urea;

N-(2,4-dimethylphenyl)-N'-[(1-phenylcyclohexyl)methyl]urea; and

N-(2,5-dimethyphenyl)-N'-[(1-phenylcyclohexyl)methyl]urea.

23. A compound as defined by claim 21 selected from the group consisting of

N-(2,4-difluorophenyl)-N'-[(1-phenylcyclohexyl)methyl]urea;

N-(2,3-dichlorophenyl)-N'-[(1-phenylcyclohexyl)methyl]urea;

N-(2,5-dichlorophenyl)-N'-[(1-phenylcyclohexyl)methyl]urea;

N-(3,4-dichlorophenyl)-N'-[(1-phenylcyclohexyl)methylurea;

N-(2,6-dibromo-4-fluorophenyl)-N'-[(1-phenylcyclohexyl)methyl]urea;

N-(5-chloro-2-methylphenyl)-N'-[(1-phenylcyclohexyl)methyl]urea;

N-[2-chloro-5-(trifluoromethyl)phenyl]-N'-[(1-phenylcyclohexyl)methyl]urea;

N-(4-chloro-2-methylphenyl)-N'-[(1-phenylcyclohexyl)methyl]urea;

N-(5-chloro-2-methoxyphenyl)-N'-[(1-phenylcyclohexyl)methyl]urea;

N-(4-chlorophenyl)-N'-[(1-phenylcyclohexyl)methyl]urea;

N-(4-bromophenyl)-N'-(1-phenylcyclohexyl)methyl]urea;

24. A compound as defined by claim 21 selected from the group consisting of

N-(3-methoxyphenyl)-N'-[(1-phenylcyclohexyl)methyl]urea;

N-(4-methoxyphenyl)-N'-[(1-phenylcyclohexyl)methyl]urea;

N-(4-ethoxyphenyl)-N'-[(1-phenylcyclohexyl)methyl]urea;

N-(4-butoxyphenyl)-N'-[(1-phenylcyclohexyl)methyl]urea;

N-(4-phenoxyphenyl)-N'-[(1-phenylcyclohexyl)methyl]urea;

N-(2,5-dimethoxyphenyl)-N'-[(1-phenylcyclohexyl)methyl]urea;

N-[(1-phenylcyclohexyl)methyl]-N'-[3-(trifluoromethyl)phenyl]urea;

N-(4-nitrophenyl)-N'-[(1-phenylcyclohexyl)methyl]urea;

N-(4-acetylphenyl)-N'-[(1-phenylcyclohexyl)methyl]urea; and

N-[(1-[1,1'-biphenyl]-4-ylcyclobutyl)methyl]N'-[2,6-bis(1-methylethyl)phenyl]urea.

25. A compound as defined by claim 21 selected from the group consisting of

N-(2,6-diethyl]phenyl)-N'-[1-(2-thienyl)cyclohexyl]urea;

N-(2,6-diethylphenyl)-N'-[1-(2-thienyl)cyclohexyl]urea;

N-[2,6-bis(1-methylethyl)]-N'-[1-(2-thienyl)cyclohexyl]urea;

N-[2-methyl-6-(1-methylethyl)phenyl]-N'-[1-(2-thienyl)cyclohexyl]urea;

N-(2,4-difluorophenyl)-N'-[1-(2-thienyl)cyclohexyl]urea; and

N-[2-(1,1-dimethylethyl)-6-methylphenyl]-N'-[1-(2-thienyl)cyclohexyl]urea.

26. A compound as defined by claim 21 selected from the group consisting of

2-[[[[(1-phenylcyclohexyl)methyl]amino]carbonyl]amino]benzoic acid, methyl ester;

2-[[[[(1-phenylcyclohexyl)methyl]amino]carbonyl]amino]benzoic acid, ethyl ester;

2-[[[[(1-phenylcyclohexyl)methyl]amino]carbonyl]amino]benzoic acid, butyl ester; and 4-[[[[(1-phenylcyclohexyl)methyl]amino]carbonyl]amino]benzoic acid, ethyl ester.

27. A compound as defined by claim 7, wherein n is 1, n' is 4 or 5, and n" is zero.

28. A compound as defined by claim 27, wherein Ar' is thienyl, tetrazolyl, isoxazolyl, triazolyl, pyrazolyl, pyridyl, or pyridyl-N-oxide.

29. A compound as defined by claim 28 selected from the group consisting of

N-[2,6-bis(1-methylethyl)phenyl]-N'-[1-[5-(1-methyltetrazolyl)cyclopentyl]methylurea;

N-[2,6-bis(1-methylethyl)phenyl]-N'-[1-[5-(1-H-tetrazolyl)cyclopentyl]methyl]urea;

N-[2,6-bis(1-methylethyl)phenyl]-N'-[1-[4-(2,5dimethylisoxazolyl)cyclopentyl]methyl]urea;

N-[2,6-bis(1-methylethyl)phenyl]-N'-[1-[4-[1-benzyl-5-(N,N-dimethyamino)]-1,2,3-triazolyl]cyclopentyl]methyl]urea;

N-[2,6-bis(1-methylethyl)phenyl]-N'-[1-[4-[1-methyl-5-(N,N-dimethylamino)-1,2,3-triazolyl]cyclopentyl]methyl]urea;

N-[2,6-bis(1-methylethyl)phenyl]—N-[1-[4-(1,3,5-trimethylpyrazolyl)cyclopentyl]methyl]urea;

N-[2,6-bis(1-methylethyl)phenyl]-N-[1-4-(1-H-3,5-dimethylpyrazolyl)cyclopentyl]methyl]urea, and N-[2,6-bis(1-methylethyl)phenyl]-N'-[1-(3pyridyl)cyclopentyl]methyl]urea-3—N-oxide.

30. A pharmaceutical composition for regulating cholesterol comprising an ACAT-inhibitory effective amount of a compound as defined by claim 1 in combination with a pharmaceutically acceptable carrier.

31. A method of treating hypercholesterolemia and atherosclerosis comprising administering to a patient an ACAT-inhibitory effective amount of a compound as defined by claim 1 in combination with a pharmaceutically acceptable carrier.

* * * * *